United States Patent
Moller et al.

(10) Patent No.: US 8,353,878 B2
(45) Date of Patent: Jan. 15, 2013

(54) INJECTION DEVICE COMPRISING A LOCKING NUT

(75) Inventors: Claus Schmidt Moller, Fredensborg (DK); Lars Peter Klitmose, Gentofte (DK); Claus Urup Gjoedesen, Copenhagen O (DK)

(73) Assignee: Novo Nordisk A/S, Bagsvaerd (DK)

( * ) Notice: Subject to any disclaimer, the term of this patent is extended or adjusted under 35 U.S.C. 154(b) by 418 days.

(21) Appl. No.: 12/532,337

(22) PCT Filed: Mar. 14, 2008

(86) PCT No.: PCT/EP2008/053103
§ 371 (c)(1),
(2), (4) Date: Dec. 21, 2009

(87) PCT Pub. No.: WO2008/116766
PCT Pub. Date: Oct. 2, 2008

(65) Prior Publication Data
US 2010/0114025 A1    May 6, 2010

Related U.S. Application Data

(60) Provisional application No. 60/928,324, filed on May 9, 2007.

(30) Foreign Application Priority Data

Mar. 23, 2007   (EP) .................................. 07104819

(51) Int. Cl.
*A61M 5/00* (2006.01)
(52) U.S. Cl. ...................................................... 604/207
(58) Field of Classification Search ........... 604/207–211
See application file for complete search history.

(56) References Cited

U.S. PATENT DOCUMENTS 854,399 A    5/1907    Bridge
(Continued)

FOREIGN PATENT DOCUMENTS

AU    2003232576    1/2004
(Continued)

OTHER PUBLICATIONS

Chia Kai Su et al, Process Biochemistry, 2006, vol. 41, Part 2, pp. 257-263.

(Continued)

*Primary Examiner* — Kevin C Sirmons
*Assistant Examiner* — Deanna K Hall
(74) *Attorney, Agent, or Firm* — Wesley A. Nicolas; Marc A. Began; Reza Green

(57) ABSTRACT

The invention relates to an injection device for injecting a dose of drug. The injection device comprises a housing, a dose setting mechanism being operable to set a desired dose, an injection mechanism comprising a piston rod (7) adapted to cooperate with a piston positioned in a cartridge containing a drug to be delivered in order to cause a set dose to be delivered from the cartridge via the injection device, a dosage tube (6), and retaining means arranged to prevent axial movement of the dosage tube in a distal direction relatively to the housing during dose setting. The dose setting mechanism comprises a rotatable dose knob (24), operation of the dose setting mechanism causing energy to be stored in a spring member. The injection mechanism is driven by releasing energy previously stored in the spring member during dose setting.

14 Claims, 15 Drawing Sheets

U.S. PATENT DOCUMENTS

| | | | |
|---|---|---|---|
| 2,392,196 A | 2/1946 | Smith | |
| 2,956,563 A | 10/1960 | Sarnoff | |
| 3,110,310 A | 11/1963 | Cislak | |
| 3,115,135 A | 12/1963 | Sarnoff | |
| 3,144,178 A | 8/1964 | Sarnoff et al. | |
| 3,556,099 A | 1/1971 | Knight et al. | |
| 3,880,162 A | 4/1975 | Simmons | |
| 3,944,843 A | 3/1976 | Vaz Martins | |
| 4,026,288 A | 5/1977 | Costa et al. | |
| 4,231,368 A | 11/1980 | Becker | |
| 4,275,727 A | 6/1981 | Keeri-Szanto | |
| 4,277,227 A | 7/1981 | Jenkins | |
| 4,298,000 A | 11/1981 | Thill et al. | |
| 4,300,554 A | 11/1981 | Hessberg et al. | |
| 4,313,439 A | 2/1982 | Babb et al. | |
| 4,314,556 A | 2/1982 | Ma | |
| 4,368,731 A | 1/1983 | Schramm | |
| RE31,315 E | 7/1983 | Jenkins et al. | |
| 4,393,723 A | 7/1983 | Brand | |
| 4,430,079 A | 2/1984 | Thill et al. | |
| 4,465,478 A | 8/1984 | Sabelman et al. | |
| 4,470,317 A | 9/1984 | Sabloewski et al. | |
| 4,493,704 A | 1/1985 | Beard et al. | |
| 4,498,904 A | 2/1985 | Turner et al. | |
| 4,515,584 A | 5/1985 | Abe et al. | |
| 4,568,335 A | 2/1986 | Updike et al. | |
| 4,585,439 A | 4/1986 | Michel | |
| 4,634,431 A | 1/1987 | Whitney et al. | |
| 4,676,122 A | 6/1987 | Szabo et al. | |
| 4,749,109 A | 6/1988 | Kamen | |
| 4,812,724 A | 3/1989 | Langer et al. | |
| 4,833,379 A | 5/1989 | Kaibel et al. | |
| 4,838,860 A | 6/1989 | Groshong et al. | |
| 4,865,591 A | 9/1989 | Sams | |
| 4,871,351 A | 10/1989 | Feingold | |
| 4,883,472 A | 11/1989 | Michel | |
| 4,893,291 A | 1/1990 | Bick et al. | |
| 4,898,578 A | 2/1990 | Rubalcaba | |
| 4,919,596 A | 4/1990 | Slate et al. | |
| 4,936,833 A | 6/1990 | Sams | |
| 4,950,246 A | 8/1990 | Muller | |
| 4,973,318 A | 11/1990 | Holm | |
| 4,988,337 A | 1/1991 | Ito | |
| 4,994,033 A | 2/1991 | Shockey et al. | |
| 5,000,744 A | 3/1991 | Hoffman et al. | |
| 5,002,537 A | 3/1991 | Hoffman et al. | |
| 5,064,098 A | 11/1991 | Hutter et al. | |
| 5,078,698 A | 1/1992 | Stiehl et al. | |
| 5,104,380 A | 4/1992 | Holman et al. | |
| 5,104,388 A | 4/1992 | Quackenbush | |
| 5,113,869 A | 5/1992 | Nappholz et al. | |
| 5,114,406 A | 5/1992 | Gabriel et al. | |
| 5,135,485 A | 8/1992 | Cohen et al. | |
| 5,163,904 A | 11/1992 | Lampropoulos et al. | |
| 5,176,646 A | 1/1993 | Kuroda | |
| 5,207,752 A | 5/1993 | Sorenson et al. | |
| 5,221,268 A | 6/1993 | Barton et al. | |
| 5,226,342 A | 7/1993 | Panin | |
| 5,226,895 A | 7/1993 | Harris | |
| 5,226,896 A | 7/1993 | Harris | |
| 5,244,461 A | 9/1993 | Derlien | |
| 5,244,465 A | 9/1993 | Michel | |
| 5,246,417 A | 9/1993 | Haak et al. | |
| 5,257,987 A | 11/1993 | Athayde et al. | |
| 5,271,527 A | 12/1993 | Haber et al. | |
| 5,279,585 A | 1/1994 | Balkwill | |
| 5,279,586 A | 1/1994 | Balkwill | |
| 5,281,198 A | 1/1994 | Haber et al. | |
| 5,284,480 A | 2/1994 | Porter et al. | |
| 5,292,976 A | 3/1994 | Dessau et al. | |
| 5,295,976 A | 3/1994 | Harris | |
| 5,304,152 A | 4/1994 | Sams | |
| 5,308,340 A | 5/1994 | Harris | |
| 5,314,412 A | 5/1994 | Rex | |
| 5,318,540 A | 6/1994 | Athayde et al. | |
| 5,320,609 A | 6/1994 | Haber et al. | |
| 5,331,954 A | 7/1994 | Rex et al. | |
| 5,368,572 A | 11/1994 | Shirota | |
| 5,370,629 A | 12/1994 | Michel et al. | |
| 5,378,233 A | 1/1995 | Haber et al. | |
| 5,383,856 A | 1/1995 | Bersin | |
| 5,383,865 A | 1/1995 | Michel | |
| 5,440,976 A | 8/1995 | Giuliano et al. | |
| 5,445,606 A | 8/1995 | Haak et al. | |
| 5,447,150 A | 9/1995 | Bacon | |
| 5,478,316 A | 12/1995 | Bitdinger et al. | |
| 5,480,387 A | 1/1996 | Gabriel et al. | |
| 5,492,534 A | 2/1996 | Athayde et al. | |
| 5,496,286 A | 3/1996 | Stiehl et al. | |
| 5,505,697 A | 4/1996 | McKinnon, Jr. et al. | |
| 5,505,704 A | 4/1996 | Pawelka et al. | |
| 5,536,249 A | 7/1996 | Castellano et al. | |
| 5,546,932 A | 8/1996 | Galli | |
| 5,549,575 A | 8/1996 | Giambattista | |
| 5,573,729 A | 11/1996 | Belgardt et al. | |
| 5,582,598 A | 12/1996 | Chanoch | |
| 5,584,815 A | 12/1996 | Pawelka et al. | |
| 5,591,136 A | 1/1997 | Gabriel | |
| 5,593,390 A | 1/1997 | Castellano et al. | |
| 5,599,314 A | 2/1997 | Neill | |
| 5,611,783 A | 3/1997 | Mikkelsen | |
| 5,611,784 A | 3/1997 | Barresi et al. | |
| 5,626,566 A | 5/1997 | Petersen et al. | |
| 5,628,309 A | 5/1997 | Brown | |
| 5,637,095 A | 6/1997 | Nason et al. | |
| 5,645,052 A | 7/1997 | Kersey | |
| 5,662,612 A | 9/1997 | Niehoff | |
| 5,674,204 A | 10/1997 | Chanoch | |
| 5,679,111 A | 10/1997 | Hertman et al. | |
| 5,681,285 A | 10/1997 | Ford et al. | |
| 5,685,864 A | 11/1997 | Shanley et al. | |
| 5,688,251 A | 11/1997 | Chanoch | |
| 5,709,662 A | 1/1998 | Olive et al. | |
| 5,716,990 A | 2/1998 | Bagshawe et al. | |
| 5,720,733 A | 2/1998 | Brown | |
| 5,725,508 A | 3/1998 | Chanoch | |
| 5,728,074 A | 3/1998 | Castellano et al. | |
| 5,728,559 A | 3/1998 | Nilsson et al. | |
| 5,741,211 A | 4/1998 | Renirie et al. | |
| 5,743,889 A | 4/1998 | Sams | |
| 5,755,692 A | 5/1998 | Manicom | |
| 5,782,633 A | 7/1998 | Mühlbauer | |
| 5,807,334 A | 9/1998 | Hodosh et al. | |
| 5,814,022 A | 9/1998 | Antanavich et al. | |
| 5,820,602 A | 10/1998 | Kovelman et al. | |
| 5,823,998 A | 10/1998 | Yamagata | |
| 5,827,232 A | 10/1998 | Chanoch | |
| 5,843,036 A | 12/1998 | Olive et al. | |
| 5,879,360 A | 3/1999 | Crankshaw | |
| 5,879,630 A | 3/1999 | Lescouzeres et al. | |
| 5,882,718 A | 3/1999 | Pommer et al. | |
| 5,898,028 A | 4/1999 | Jensen et al. | |
| 5,921,966 A | 7/1999 | Bendek et al. | |
| 5,928,201 A | 7/1999 | Poulsen et al. | |
| 5,933,671 A | 8/1999 | Stephany et al. | |
| 5,938,642 A | 8/1999 | Burroughs et al. | |
| 5,947,934 A | 9/1999 | Hansen et al. | |
| 5,951,530 A | 9/1999 | Steengaard et al. | |
| 5,954,689 A | 9/1999 | Poulsen | |
| 5,954,700 A | 9/1999 | Kovelman | |
| 5,957,889 A | 9/1999 | Poulsen et al. | |
| 5,961,496 A | 10/1999 | Nielsen et al. | |
| 5,971,963 A | 10/1999 | Choi | |
| 5,980,491 A | 11/1999 | Hansen | |
| 5,984,900 A | 11/1999 | Mikkelsen | |
| 5,989,221 A | 11/1999 | Hjertman | |
| 5,998,989 A | 12/1999 | Lohberg | |
| 6,003,736 A | 12/1999 | Ljunggren | |
| 6,004,297 A | 12/1999 | Steenfeldt-Jensen | |
| 6,010,485 A | 1/2000 | Buch-Rasmussen et al. | |
| 6,019,745 A | 2/2000 | Gray | |
| 6,033,376 A | 3/2000 | Rockley | |
| 6,033,377 A | 3/2000 | Rasmussen et al. | |
| 6,036,675 A | 3/2000 | Thorne et al. | |
| 6,048,336 A | 4/2000 | Gabriel | |
| 6,074,372 A | 6/2000 | Hansen et al. | |
| 6,083,197 A | 7/2000 | Umbaugh | |

| | | | | | | |
|---|---|---|---|---|---|---|
| 6,086,567 | A | 7/2000 | Kirchhofer et al. | 2002/0049415 A1 | 4/2002 | Fukuda |
| 6,096,010 | A | 8/2000 | Walters | 2002/0052578 A1 | 5/2002 | Moller |
| 6,110,148 | A | 8/2000 | Brown et al. | 2002/0077852 A1 | 6/2002 | Ford et al. |
| 6,110,149 | A | 8/2000 | Klitgaard et al. | 2002/0107486 A1 | 8/2002 | Munk |
| 6,129,080 | A | 10/2000 | Pitcher et al. | 2002/0120235 A1 | 8/2002 | Enggaard |
| 6,146,361 | A | 11/2000 | DiBiasi et al. | 2002/0165500 A1 | 11/2002 | Bechtold et al. |
| 6,159,161 | A | 12/2000 | Hodosh | 2002/0173752 A1 | 11/2002 | Polzin |
| 6,161,364 | A | 12/2000 | Kolberg | 2002/0188250 A1 | 12/2002 | Landau et al. |
| 6,193,698 | B1 | 2/2001 | Kirchhofer et al. | 2003/0009133 A1 | 1/2003 | Ramey |
| 6,221,046 | B1 | 4/2001 | Burroughs et al. | 2003/0039679 A1 | 2/2003 | Duirs |
| 6,221,053 | B1 | 4/2001 | Walters | 2003/0073954 A1 | 4/2003 | Moberg et al. |
| 6,231,540 | B1 | 5/2001 | Smedegaard | 2003/0114800 A1 | 6/2003 | Veasey et al. |
| 6,235,004 | B1 | 5/2001 | Steenfeldt-Jensen et al. | 2003/0172924 A1 | 9/2003 | Staniforth et al. |
| 6,245,046 | B1 | 6/2001 | Sibbitt | 2003/0176871 A1 | 9/2003 | Pavlov et al. |
| 6,248,090 | B1 | 6/2001 | Jensen et al. | 2003/0216663 A1 | 11/2003 | Jersey-Willuhn et al. |
| 6,248,095 | B1 | 6/2001 | Giambatista et al. | 2003/0233075 A1 | 12/2003 | Huegli |
| 6,258,062 | B1 | 7/2001 | Thielen et al. | 2004/0010204 A1 | 1/2004 | Weber et al. |
| 6,268,722 | B1 | 7/2001 | Kogure et al. | 2004/0024361 A1 | 2/2004 | Fago |
| 6,269,340 | B1 | 7/2001 | Ford et al. | 2004/0051368 A1 | 3/2004 | Caputo et al. |
| 6,277,097 | B1 | 8/2001 | Mikkelsen et al. | 2004/0059299 A1 | 3/2004 | Moller |
| 6,277,098 | B1 | 8/2001 | Klitmose et al. | 2004/0108339 A1 | 6/2004 | Hansen et al. |
| 6,281,225 | B1 | 8/2001 | Hearst et al. | 2004/0158304 A1 | 8/2004 | Cory et al. |
| 6,283,941 | B1 | 9/2001 | Schoenfeld et al. | 2004/0171983 A1 | 9/2004 | Sparks et al. |
| 6,287,283 | B1 | 9/2001 | Ljunggreen et al. | 2004/0186431 A1 | 9/2004 | Graf et al. |
| 6,302,869 | B1 | 10/2001 | Klitgaard | 2004/0207385 A1 | 10/2004 | Gafner et al. |
| 6,312,413 | B1 | 11/2001 | Jensen et al. | 2004/0210199 A1 | 10/2004 | Atterbury et al. |
| 6,340,357 | B1 | 1/2002 | Poulsen et al. | 2004/0230157 A1 | 11/2004 | Perry et al. |
| 6,364,860 | B1 | 4/2002 | Steck et al. | 2004/0236282 A1 | 11/2004 | Braithwaite |
| 6,379,339 | B1 | 4/2002 | Klitgaard et al. | 2004/0249348 A1 | 12/2004 | Wimpenny et al. |
| 6,383,167 | B2 | 5/2002 | Kirchhofer et al. | 2004/0260247 A1 | 12/2004 | Veasey et al. |
| 6,391,005 | B1 | 5/2002 | Lum et al. | 2004/0267207 A1 | 12/2004 | Veasey et al. |
| 6,419,661 | B1 | 7/2002 | Kuhr et al. | 2004/0267208 A1 | 12/2004 | Veasey et al. |
| 6,514,230 | B1 | 2/2003 | Munk et al. | 2005/0004529 A1 | 1/2005 | Veasey et al. |
| 6,537,251 | B2 | 3/2003 | Klitmose | 2005/0019400 A1 | 1/2005 | Deveney et al. |
| 6,547,755 | B1 | 4/2003 | Lippe et al. | 2005/0033244 A1 | 2/2005 | Veasey et al. |
| 6,547,763 | B2 | 4/2003 | Steenfeldt-Jensen et al. | 2005/0055011 A1 | 3/2005 | Enggaard |
| 6,547,764 | B2 | 4/2003 | Larsen et al. | 2005/0197625 A1 | 9/2005 | Haueter et al. |
| 6,562,011 | B1 | 5/2003 | Buch-Rasmussen et al. | 2005/0205083 A1 | 9/2005 | Staniforth et al. |
| 6,569,126 | B1 | 5/2003 | Poulsen et al. | 2005/0209570 A1 | 9/2005 | Møller |
| 6,582,404 | B1 | 6/2003 | Klitgaard et al. | 2005/0268915 A1 | 12/2005 | Wassenaar et al. |
| 6,585,698 | B1 | 7/2003 | Packman et al. | 2006/0118612 A1 | 6/2006 | Christoffersen et al. |
| 6,599,272 | B1 | 7/2003 | Hjertman et al. | 2006/0258988 A1 | 11/2006 | Keitel et al. |
| 6,605,067 | B1 | 8/2003 | Larsen | 2006/0264838 A1 | 11/2006 | Volckmann |
| 6,613,019 | B2 | 9/2003 | Munk | 2007/0093761 A1 | 4/2007 | Veasey |
| 6,663,602 | B2 | 12/2003 | Moller | 2007/0244445 A1 | 10/2007 | Moller |
| 6,666,849 | B1 | 12/2003 | Marshall et al. | 2008/0065026 A1 | 3/2008 | Moller |
| 6,673,033 | B1 | 1/2004 | Sciulli et al. | 2008/0221530 A1 | 9/2008 | Glejbol et al. |
| 6,692,472 | B2 | 2/2004 | Hansen et al. | 2008/0281275 A1 | 11/2008 | Moller |
| 6,699,224 | B2 | 3/2004 | Kirchhofer et al. | 2009/0043264 A1 | 2/2009 | Glejbol et al. |
| 6,716,198 | B2 | 4/2004 | Larsen | 2009/0062748 A1 | 3/2009 | Moller et al. |
| 6,726,661 | B2 | 4/2004 | Munk et al. | | | |
| 6,752,798 | B2 | 6/2004 | McWethy et al. | | | |
| 6,770,288 | B2 | 8/2004 | Duirs | | | |
| 6,796,970 | B1 | 9/2004 | Klitmose et al. | | | |
| 6,852,404 | B2 | 2/2005 | Kuwajima et al. | | | |
| 6,887,238 | B2 | 5/2005 | Jahns et al. | | | |
| 6,893,415 | B2 | 5/2005 | Madsen et al. | | | |
| 6,899,698 | B2 | 5/2005 | Sams | | | |
| 6,899,699 | B2 | 5/2005 | Enggaard | | | |
| 6,945,961 | B2 | 9/2005 | Miller et al. | | | |
| 7,008,399 | B2 | 3/2006 | Larsen et al. | | | |
| 7,080,936 | B1 | 7/2006 | Simpson | | | |
| 7,090,662 | B2 | 8/2006 | Wimpenny et al. | | | |
| 7,094,221 | B2 | 8/2006 | Veasey et al. | | | |
| 7,104,972 | B2 | 9/2006 | Moller et al. | | | |
| 7,133,329 | B2 | 11/2006 | Skyggebjerg et al. | | | |
| 7,175,055 | B2 | 2/2007 | Hansen et al. | | | |
| 7,195,609 | B2 | 3/2007 | Huegli | | | |
| 7,195,616 | B2 | 3/2007 | Diller et al. | | | |
| 7,241,278 | B2 | 7/2007 | Moller | | | |
| 7,500,966 | B2 | 3/2009 | Hommann | | | |
| 7,678,084 | B2 | 3/2010 | Judson et al. | | | |
| 7,704,238 | B2 | 4/2010 | Diller et al. | | | |
| 2001/0034506 | A1 | 10/2001 | Hirschman et al. | | | |
| 2001/0053893 | A1 | 12/2001 | Larsen | | | |
| 2002/0002326 | A1 | 1/2002 | Causey, III et al. | | | |
| 2002/0007154 | A1 | 1/2002 | Hansen et al. | | | |
| 2002/0016571 | A1 | 2/2002 | Kirchhofer et al. | | | |
| 2002/0020654 | A1 | 2/2002 | Eilersen | | | |

FOREIGN PATENT DOCUMENTS

| | | |
|---|---|---|
| CA | 2359375 | 7/2000 |
| DE | 3048135 | 7/1982 |
| DE | 3236374 | 4/1984 |
| DE | 3609555 | 9/1987 |
| DE | 3638984 | 5/1988 |
| DE | 3923079 | 1/1991 |
| DE | 4223958 | 1/1993 |
| DE | 4419235 | 12/1995 |
| DE | 19503230 | 8/1996 |
| DE | 29513214 | 2/1997 |
| DE | 19723647 | 12/1998 |
| DE | 19838760 | 4/2000 |
| DE | 29907880 | 9/2000 |
| DE | 10103287 | 8/2001 |
| DE | 10201875 | 5/2003 |
| DE | 10229122 | 2/2004 |
| DE | 20317377 | 3/2005 |
| DE | 102004046003 | 3/2006 |
| DK | 200100240 | 2/2001 |
| DK | 2005/00116 | 6/2005 |
| EP | 15617 | 9/1980 |
| EP | 017318 | 10/1980 |
| EP | 0064858 | 11/1982 |
| EP | 327810 | 8/1989 |
| EP | 327910 | 8/1989 |
| EP | 338806 | 10/1989 |
| EP | 0362484 | 4/1990 |

| | | | | | | |
|---|---|---|---|---|---|---|
| EP | 387854 | 9/1990 | | WO | WO90/09202 | 8/1990 |
| EP | 422482 | 4/1991 | | WO | WO 9110460 | 7/1991 |
| EP | 454331 | 10/1991 | | WO | WO9110677 | 7/1991 |
| EP | 498737 | 8/1992 | | WO | WO 9114467 | 10/1991 |
| EP | 879610 | 8/1992 | | WO | WO93/01573 | 1/1993 |
| EP | 608343 | 4/1993 | | WO | WO 9303780 | 3/1993 |
| EP | 554996 | 8/1993 | | WO | WO 9307922 | 4/1993 |
| EP | 594349 | 4/1994 | | WO | WO 9412228 | 6/1994 |
| EP | 615762 | 9/1994 | | WO | WO95/24233 | 9/1995 |
| EP | 513128 | 7/1995 | | WO | WO 9607443 | 3/1996 |
| EP | 0673482 | 9/1995 | | WO | WO 9626754 | 9/1996 |
| EP | 679440 | 11/1995 | | WO | WO 96/32973 | 10/1996 |
| EP | 702970 | 3/1996 | | WO | WO 9638190 | 12/1996 |
| EP | 1000631 | 10/1997 | | WO | WO 9707841 | 3/1997 |
| EP | 554995 | 12/1997 | | WO | WO 9710865 | 3/1997 |
| EP | 295075 | 12/1998 | | WO | WO97/30742 | 8/1997 |
| EP | 897728 | 2/1999 | | WO | WO9734919 | 9/1997 |
| EP | 0937471 | 8/1999 | | WO | WO 9736626 | 10/1997 |
| EP | 0937472 | 8/1999 | | WO | WO 9810813 | 3/1998 |
| EP | 937476 | 8/1999 | | WO | WO 9856436 | 12/1998 |
| EP | 1003581 | 8/1999 | | WO | WO 9857688 | 12/1998 |
| EP | 1351732 | 1/2001 | | WO | WO99/07425 | 2/1999 |
| EP | 1074273 | 2/2001 | | WO | WO99/15214 | 4/1999 |
| EP | 1095668 | 5/2001 | | WO | WO 9916487 | 4/1999 |
| EP | 0747391 | 3/2004 | | WO | WO 9921598 | 5/1999 |
| EP | 1462134 | 9/2004 | | WO | WO 9938554 | 8/1999 |
| EP | 1541185 | 6/2005 | | WO | WO 9948546 | 9/1999 |
| EP | 1557163 | 7/2005 | | WO | WO99/65548 | 12/1999 |
| EP | 1557189 | 7/2005 | | WO | WO0037129 | 6/2000 |
| EP | 1568389 | 8/2005 | | WO | WO 00/51668 | 9/2000 |
| EP | 1304129 | 11/2005 | | WO | WO 01/10484 | 2/2001 |
| EP | 1610848 | 1/2006 | | WO | WO 01/19434 | 3/2001 |
| EP | 1645301 | 4/2006 | | WO | WO01/26710 | 4/2001 |
| EP | 1723977 | 11/2006 | | WO | WO 01/30425 | 5/2001 |
| EP | 1728529 | 12/2006 | | WO | WO0172361 | 10/2001 |
| EP | 1782853 | 5/2007 | | WO | WO 0195959 | 12/2001 |
| EP | 1819382 | 8/2007 | | WO | WO02/05876 | 1/2002 |
| EP | 2000161 | 12/2008 | | WO | WO0224257 | 3/2002 |
| FR | 2583291 | 12/1986 | | WO | WO 02/053214 | 7/2002 |
| FR | 2622457 | 5/1989 | | WO | WO02/064196 | 8/2002 |
| FR | 2697434 | 5/1994 | | WO | WO 02/076535 | 10/2002 |
| FR | 2740345 | 4/1997 | | WO | WO 02076536 | 10/2002 |
| FR | 2767479 | 2/1999 | | WO | WO02092153 | 11/2002 |
| FR | 2857654 | 1/2005 | | WO | WO03/057283 | 7/2003 |
| GB | 664044 | 1/1952 | | WO | WO03/063680 | 8/2003 |
| GB | 2091107 | 7/1982 | | WO | WO97/33638 | 9/2003 |
| GB | 2153445 | 8/1985 | | WO | WO 03080160 | 10/2003 |
| GB | 2229497 | 9/1990 | | WO | WO03/099357 | 12/2003 |
| GB | 2309644 | 8/1997 | | WO | WO 2004/002556 | 1/2004 |
| GB | 0007071.4 | 3/2000 | | WO | WO 2004004825 | 1/2004 |
| IN | 165367 | 3/1986 | | WO | WO 2004007002 | 1/2004 |
| JP | 56-163486 | 12/1981 | | WO | WO 2004/024218 | 3/2004 |
| JP | 57-000033 | 1/1982 | | WO | WO 2004/028598 | 4/2004 |
| JP | 01-100495 | 4/1989 | | WO | WO 2004035113 | 4/2004 |
| JP | 64-035671 | 6/1989 | | WO | WO 2004/078240 | 9/2004 |
| JP | 02-126184 | 5/1990 | | WO | WO2004/080306 | 9/2004 |
| JP | 02-182267 | 7/1990 | | WO | WO 2004078239 | 9/2004 |
| JP | 4-224764 | 8/1992 | | WO | WO 2004078241 | 9/2004 |
| JP | 4-507059 | 12/1992 | | WO | WO 2004078242 | 9/2004 |
| JP | 05-337179 | 12/1993 | | WO | WO2004/084795 | 10/2004 |
| JP | 06-055644 | 1/1994 | | WO | WO2004/095379 | 11/2004 |
| JP | 7-500039 | 3/1994 | | WO | WO 2005018721 | 3/2005 |
| JP | 06-034825 | 10/1994 | | WO | WO 2005037352 | 4/2005 |
| JP | 06-296691 | 10/1994 | | WO | WO 2005/046770 | 5/2005 |
| JP | 7-502678 | 3/1995 | | WO | WO2005/089835 | 9/2005 |
| JP | 09166474 | 6/1997 | | WO | WO 2005097233 | 10/2005 |
| JP | 3017167 | 11/1999 | | WO | WO 2005097240 | 10/2005 |
| JP | 2000237308 | 9/2000 | | WO | WO 2006/039930 | 4/2006 |
| JP | 2003284777 | 10/2003 | | WO | WO2006/045425 | 5/2006 |
| JP | 2004-503303 | 2/2004 | | WO | WO2006/045525 | 5/2006 |
| JP | 2004-516895 | 6/2004 | | WO | WO 2006/045528 | 5/2006 |
| JP | 2006250582 | 9/2006 | | WO | WO 2006/045529 | 5/2006 |
| JP | 2007-509662 | 4/2007 | | WO | WO 2006045529 A1 * | 5/2006 |
| RU | 2111019 | 5/1997 | | WO | WO 2006/069454 | 7/2006 |
| RU | 2091087 | 9/1997 | | WO | WO2006/076921 | 7/2006 |
| RU | 2212254 | 9/2003 | | WO | WO2006/116997 | 11/2006 |
| WO | WO 85/02256 | 5/1985 | | WO | WO 2006/128794 | 12/2006 |
| WO | WO 8702895 | 5/1987 | | WO | WO 2007/030957 | 3/2007 |
| WO | WO 8907463 | 8/1989 | | WO | WO2007/041843 | 4/2007 |

| WO | WO2007/107558 | 9/2007 |
| WO | WO2007/107561 | 9/2007 |
| WO | WO 2007/134954 | 11/2007 |
| WO | WO 2008/037801 | 4/2008 |
| WO | WO2008057223 | 5/2008 |

OTHER PUBLICATIONS

Dennison, Clive et al, Protein Expression and Purification, 1997, vol. 11, Part 2, pp. 149-161.
Fransson et al, Pharmaceutical Research, 1997, vol. 14, Part 5, pp. 606-612.
International Search Report and Written Opinion Issued in Connection With PCT Application No. PCT/EP2006/061747, Mailed Sep. 29, 2006.
International Search Report and Written Opinion Issued in Connection With PCT Application No. PCT/EP2006/061748, Mailed Aug. 10, 2006.
Leonil et al, Enzyme and Microbiol Technology, 1994, vol. 16, Part 7, pp. 591-595.
Owen Mumford Product Range.
Paule, B.J.A. et al, Protein Expression and Purification, 2004, vol. 34, Part 2, pp. 311-316.
Search Report Issued in Connection With Danish Application No. PA 2005 00588, Mailed Feb. 13, 2006.
Search Report Issued in Connection With Danish Application No. PA 2005 00589, Mailed Feb. 16, 2006.
Search Report Issued in Connection With European Application No. 06005599.3, Mailed Oct. 4, 2006.
Search Report Issued in Connection With PCT Application No. PCT/EP2007/052633, Mailed Feb. 20, 2008.
English Abstract of DE 19838760 Dated Apr. 20, 2000.
English Abstract of DE29513214 Published Feb. 13, 1997.
English Abstract of DE3048135 Published Jul. 15, 1982.
Machine Translation of DE3609555TX.
Machine Translation of EP679440TX.
Machine Translation of FR2583291TX.
English Abstract of FR2622457 Published May 5, 1989.
English Abstract of FR2697434 Published May 6, 1994.
English Abtsract of JP4-507059 Published Dec. 10, 1992.
English Abstract of JP06-034825 Published Oct. 2, 1994.
English Abstract of JP06-055644 Published Jan. 3, 1994.
English Abstract of JP57-000033.
English Abstract of JP64-035671 Published Jun. 2, 1989.
English Abstract of JP 7-500039 Published Mar. 14, 1994.
English Abstract for JP 2000237308.
English Abstract for JP 2003284777.
English Abstract for RU2111019.
Notice of Opposition by Owen Mumford (UK).
Notice of Opposition by Genentech (USA).
Notice of Opposition by Techpharma (CH) Including English Translation.
Validity Opinion by the UK PTO.
Written Opinion Issued in Connection With PCT Application No. PCT/EP2006/061747, Mailed Nov. 8, 2006.
Written Opinion Issued in Connection With PCT Application No. PCT/EP2006/061748, Mailed Nov. 8, 2006.
Non-Final Rejection of Oct. 7, 2008 in U.S. Appl. No. 10/508,104,(US Patent No. 7,678,084; Issue Date Mar. 16, 2010) filed Sep. 15, 2004; First Named Inventor: Jared Alden Judson.
Non-Final Rejection of Mar. 19, 2009 in U.S. Appl. No. 10/508,104, (US Patent No. 7,678,084; Issue Date Mar. 16, 2010) filed Sep. 15, 2004; First Named Inventor: Jared Alden Judson.
Office Action Mailed Jul. 20, 2010 in U.S. Appl. No. 12/300,675, filed May 3, 2007 by Moller et al.
Office Action Mailed Feb. 3, 2011 in U.S. Appl. No. 12/300,675, filed May 3, 2007 by Moller et al.
Office Action Mailed Dec. 27, 2010 in U.S. Appl. No. 12/442,168, filed March 20, 2009 by Moller et al.
Beckmann, Sensors, Memory, Circuits, Polyapply Newsletter, vol. 1(3) (2006).
Trankler, Hans-Rolf, R. Oldenbourg, Verlag, Munchen, Wien.
English Abstract of DE10201875.
English Abstract of DE102004046003.
English Abstract of DE19503230.
English Abstract of DE3923079.
English Abstract of DE3236374.
English Abstract of EP387854.
English Abstract of EP422482.
English Abstract of FR2622457.
English Abstract of FR2740345.
English Abstract of IN165367.
Machine Translation of JP09166474.
English Abstract of JP2006250582.
English Abstract of JP02-126184.
English Abstract of TP56-163486.
English Abstract of JP3017167.
English Abstract of JP01-100495.
English Abstract of JP02-182267.
Common Insulin Injection Challenges: http://www.hd.com/us/diabetes/p..aspx?cat-7001&id-7265.
Gnanalingham, M.G. et al., Accuracy and Reproducibility of Low Dose Insulin Administration Using Pen-Injectors and Syringes, Downloaded From ADC.BMJ.COM on Jan. 9, 2008.
Annersten, M. et al., Insulin Pens Dribble From the Tip of the Needle After Injection, Practical Diabetes Int., vol. 17(4), pp. 109-111 (2000).
Office Action in U.S. Appl. No. 09/137,014, filed Aug. 20, 1998; Inventors: Jensen et al., of Jul. 9, 1999.
Office Action in U.S. Appl. No. 09/137,014, filed Aug. 20, 1998; Inventors: Jensen et al., of Feb. 18, 2000.
Office Action in U.S. Appl. No. 10/076,025, filed Feb. 13, 2002; Inventors: Larsen et al., of Nov. 28, 2003.
Office Action in U.S. Appl. No. 10/076,025, filed Feb. 13, 2002; Inventors: Larsen et al., of Nov. 15, 2004.
Office Action in U.S. Appl. No. 12/293,247, filed Sep. 16, 2008; Inventor: Andre Larsen, of Nov. 25, 2009.
Final Action in U.S. Appl. No. 12/293,247, filed Sep. 16, 2008; Inventor: Andre Larsen, of Jun. 7, 2010.
Opposition in Related European Patent Application EP 02711784.5 of Sep. 19, 2008.
Search Report Issued in Connection With European Appln No. 06005602.5, Mailed Otctober 16, 2006.
Search Report Issued in Connection With PCT Appln. No. PCT/EP2007/052630, Mailed Nov. 12, 2007.

* cited by examiner

INJECTION DEVICE COMPRISING A LOCKING NUT

CROSS-REFERENCE TO RELATED APPLICATIONS

This application is a 35 U.S.C. §371 national stage application of International Patent Application PCT/EP2008/053103 (published as WO 2008/116766), filed Mar. 14, 2008, which claimed priority of European Patent Application 07104819.3, filed Mar. 23, 2007; this application further claims priority under 35 U.S.C. §119 of U.S. Provisional Application No. 60/928,324, filed May 9, 2007.

FIELD OF THE INVENTION

The present invention relates to an injection device comprising a dose setting mechanism and an injection mechanism, the injection device preferably being of a kind which is suitable for performing self injection of a drug, such as insulin or growth hormone. More particularly, the present invention relates to an injection device as defined above in which the axial position of a piston rod can be controlled in a very accurate manner, and in which the piston rod can easily be returned to an initial position during cartridge replacement.

BACKGROUND OF THE INVENTION

US 2004/0267207 discloses a drive mechanism suitable for use in drug delivery devices. The drive mechanism may include a housing, a piston rod, and a unidirectional coupling between the housing and the piston rod. The drive mechanism may also include a dose dial sleeve and a drive sleeve, with a clutch mean located there between to prevent relative rotation between the dial sleeve and the drive sleeve when in a coupled state and to permit relative rotation between the dial sleeve and the drive sleeve when in a de-coupled state. The device may further comprise a nut being splined to the dose dial sleeve. The relative rotation between the dose dial sleeve and the drive sleeve thereby causes the nut to precess along a helical thread of the drive sleeve. The position of the nut along the helical thread corresponds to the amount of medicinal product remaining in the cartridge.

EP 0 338 806 discloses a syringe in which energy is stored in a spring during dose setting. During injection the stored energy is released, thereby causing a gear to rotate. The gear is threadedly connected to a piston rod, and rotation of the gear therefore drives the piston rod in an axial direction, thereby causing a set dose to be injected.

SUMMARY OF THE INVENTION

It is, thus, an object of the invention to provide a spring driven injection device in which the axial position of the piston rod can be controlled in a more accurate manner than in similar prior art devices.

It is a further object of the invention to provide a spring driven injection device in which it is possible to stop movements of the piston rod in a more accurate manner than in similar prior art devices.

It is an even further object of the invention to provide a spring driven injection device in which the risk of jamming of the injection device during injection is minimised.

It is an even further object of the invention to provide a spring driven injection device in which the piston rod can easily be returned to an initial position during cartridge replacement.

According to the invention the above and other objects are fulfilled by providing an injection device for injecting a dose of drug, the injection device comprising:

a housing, a dose setting mechanism being operable to set a desired dose, the dose setting mechanism comprising a rotatable dose knob, operation of the dose setting mechanism causing energy to be stored in a spring member, an injection mechanism comprising a piston rod adapted to cooperate with a piston positioned in a cartridge containing a drug to be delivered in order to cause a set dose to be delivered from the cartridge via the injection device, the injection mechanism being driven by releasing energy previously stored in the spring member during dose setting, a dosage tube being axially movable in a proximal direction relatively to the housing during dose setting and being axially movable in a distal direction relatively to the housing during injection of a set dose, and retaining means arranged to prevent axial movement of the dosage tube in a distal direction relatively to the housing during dose setting.

In the present context the term 'injection device' should be interpreted to mean a device which is suitable for injecting a drug, such as a liquid drug, into a human or animal body. The injection device is preferably of the kind being suitable for performing repetitive self injection of drug, e.g. insulin for persons having diabetes, or growth hormone. The injection device may be in the form of an injection pen, i.e. of a kind having an elongated shape similar to that of an ordinary pen.

As mentioned above, the drug is preferably a liquid drug suitable for injection into a human or animal body, e.g. subcutaneously or intravenously. Alternatively, the drug may be a dry drug which has to be reconstituted prior to injection.

The housing is a part of the injection device which at least substantially encloses the remaining parts of the injection device. Thus, the housing defines an outer boundary of the injection device. The housing may be substantially closed, i.e. it may have substantially solid walls, or it may comprise more or less open parts, such as openings, grids, etc.

The dose setting mechanism is the part of the injection device which is used for setting a desired dose. It may advantageously comprise a part which can be manipulated by an operator and one or more parts which ensure(s) that when an operator manipulates the relevant part, then the injection device is set in such manner that when the injection mechanism is subsequently operated, the desired dose is actually injected by the injection device. The operator operates the dose setting mechanism by rotating a rotatable dose knob.

The injection mechanism is the part of the injection device which is used for injecting a desired dose once is has been set by means of the dose setting mechanism. The injection mechanism comprises a piston rod, and the piston rod is adapted to cooperate with a piston positioned in a cartridge. This typically takes place by causing the piston rod to move in an axial direction in the injection device during injection of a previously set dose. The piston rod is typically arranged in the injection device in such a manner that it abuts the piston arranged in the cartridge, and axial movement of the piston rod will therefore cause corresponding axial movement of the piston in the cartridge. Thereby drug is expelled from the cartridge and injected by the injection device. The injection mechanism preferably comprises a part which can be operated by an operator, e.g. an injection button or a release mechanism, e.g. for releasing energy which was previously stored in the spring member during dose setting.

The dosage tube is axially movable in a proximal direction relatively to the housing during dose setting, and it is axially movable in a distal direction relatively to the housing during injection of a set dose. In the present context the term 'distal direction' should be interpreted to mean a direction substantially along a longitudinal axis of the injection device, and towards an end being adapted to receive an injection needle. Similarly, in the present context the term 'proximal direction' should be interpreted to mean a direction substantially along the longitudinal axis of the injection device, and substantially opposite to the distal direction, i.e. away from the end being adapted to receive an injection needle. The proximal direction is preferably in a direction towards the position of the rotatable dose knob.

The dosage tube is preferably connected to the rotatable dose knob in such a manner that rotating the dose knob causes the dosage tube to move axially in a proximal direction. Furthermore, the dosage tube is preferably connected to the spring member in such a manner that moving the dosage tube axially in a proximal direction causes energy to be stored in the spring member, and in such a manner that releasing energy stored in the spring member causes axial movement of the dosage tube in a distal direction. Finally, the dosage tube is preferably connected to the piston rod in such a manner that axial movement of the dosage tube in a distal direction causes the piston rod to cooperate with the piston to cause a set dose to be delivered.

The retaining means is arranged to prevent axial movement of the dosage tube in a distal direction relatively to the housing during injection of a set dose. In the case that the dosage tube is connected to the spring member and the piston rod as described above, the retaining means, thus, prevents the spring member from releasing the stored energy and cause the piston rod to cooperate with the piston to inject drug during dose setting. Thus, it is prevented that drug is accidentally spilled, and it is ensured that a correct dose is being set. Controlling this by axially retaining the dosage tube rather than locking the piston rod directly has the following advantage. When a cartridge is empty and therefore has to be replaced, it is necessary to return the piston rod to an initial position corresponding to a full cartridge. In the case that axial movement of the piston rod in a distal direction during dose setting is prevented by directly locking the piston rod, e.g. by means of a locking item or a locking nut, it may be difficult to return the piston rod during replacement of the cartridge. This is particularly the case when the piston rod and the locking item/locking nut are engaged in such a manner that they tend to jam. However, according to the present invention axial movement of the piston rod in a distal direction is prevented by axially retaining the dosage tube, and the risk of jamming the piston rod during replacement of the cartridge is thereby minimised, since the piston rod is allowed to return freely to the initial position.

The retaining means may be a locking nut being axially fixed relatively to the housing, and the locking nut may be adapted to be rotationally locked relatively to the housing during dose setting, and it may be adapted to be able to perform rotational movement relatively to the housing during injection of a set dose. According to this embodiment, when the locking nut is rotationally locked relatively to the housing, it axially retains the dosage tube, i.e. it prevents the dosage tube from performing axial movements in a distal direction. However, when the locking nut is allowed to perform rotational movement relatively to the housing it allows the dosage tube to move axially in a distal direction.

The locking nut and the dosage tube may be connected via mating threads formed on the dosage tube and the locking nut, respectively. According to this embodiment the dosage tube can be moved axially in a proximal direction by rotating the dosage tube, thereby allowing it to climb the threaded connection between the locking nut and the dosage tube. However, the threaded connection prevents that the dosage tube is pushed in a purely axial movement in a distal direction as long as the locking nut is not allowed to rotate relatively to the housing. When the locking nut is subsequently allowed to rotate, the dosage tube is allowed to move axially in a distal direction while causing the locking nut to rotate.

The injection device may further comprise a locking item being movable between a locking position in which it prevents the locking nut from rotating relatively to the housing, and an unlocking position in which the locking nut is allowed to rotate relatively to the housing. According to this embodiment the locking item is in its locking position during dose setting and in its unlocking position during injection of a set dose. Mating teeth may be formed on the locking nut and the locking item, respectively, and these mating teeth may engage when the locking item is in the locking position. When the locking item is moved into its unlocking position, the mating teeth are, in this case, moved out of engagement, thereby allowing mutual rotational movement between the locking nut and the locking item.

The locking item may be moved from the locking position to the unlocking position in response to operation of the injection mechanism. According to this embodiment, the locking item is automatically moved into the unlocking position when a user operates the injection mechanism. Thereby the injection device is automatically shifted from a state where a dose can be set into a state where a dose can be injected when the user operates the injection mechanism. Thereby the user only has to perform a single operation in order to cause a set dose to be injected, and the injection device is thereby very easy to operate.

As an alternative to a locking nut, the retaining means may, e.g., be or comprise a key and groove connection, one or more braking elements, one or more slidable locking elements, and/or any other means being suitable for axially retaining the dosage tube as described above during dose setting.

The dosage tube may be prevented from performing rotational movements relatively to the housing during injection of a set dose. According to this embodiment the dosage tube moves in a purely axial manner relatively to the housing during injection of a set dose. This provides a very simple movement pattern, and the risk that the injection device jams during injection of a set dose is minimised.

The dosage tube and the piston rod may be connected via mating threads formed on the dosage tube and the piston rod, respectively. According to this embodiment, the dosage tube is preferably moved along this threaded connection during dose setting. During injection the piston rod is preferably moved along the dosage tube in an axial movement.

In a preferred embodiment the dosage tube is threadedly connected to the piston rod as well as to a locking nut. For instance, the dosage tube may comprise an inner thread arranged to engage an outer thread of the piston rod and an outer thread arranged to engage an inner thread of the locking nut. According to this embodiment, the piston rod, the dosage tube and the locking nut are preferably arranged relatively to each other in such a manner that at least part of the dosage tube surrounds at least part of the piston rod, and at least part of the locking nut surrounds at least part of the dosage tube. As an alternative, the piston rod may be hollow, and the dosage tube may, in this case comprise an outer thread arranged to engage an inner thread of the hollow piston rod.

The injection device may further comprise means for preventing rotational movement of the piston rod during dose setting. The means for preventing rotational movement of the piston rod may comprise a key and groove connection between the piston rod and a member being fixed relatively to the housing. Such a key and groove connection prevents the piston rod from rotating relatively to the housing, but relative axial movement is possible. The member is fixed relatively to the housing during normal operation, i.e. at least when a cartridge is inserted in the housing. However, the member may advantageously be fixed to the housing in such a manner that it is released, e.g. allowing rotational movements of the member relatively to the housing, during change of cartridge. Such an arrangement would allow the piston rod to be moved back during change of cartridge. This will be explained in more detail below with reference to the drawings.

Alternatively, the means for preventing rotational movement of the piston rod may comprise a third thread connection provided between the piston rod and a member being fixed relatively to the housing. The remarks set forth above relating to the member being fixed to the housing are equally applicable here. The third thread connection preferably has a pitch being directed in a direction which is opposite to the direction of the first thread. According to this embodiment the first thread connection between the locking nut and the piston rod and the third thread connection between the member and the piston rod in combination prevent rotational movement of the piston rod during dose setting, and thereby prevent axial movement of the piston rod during dose setting.

The dosage tube may further be threadedly connected to the dose knob via a second thread connection. According to this embodiment the dosage tube is preferably rotated along the second thread connection during setting of a dose.

As an alternative, the dosage tube may be connected to the dose knob via a key and groove connection. In this case the dosage tube is simply rotated along with the dose knob during dose setting, and the dose knob and the dosage tube are allowed to perform mutual axial movements.

The operation of the dose setting mechanism causes energy to be stored in a spring member, and the injection mechanism is driven by releasing energy previously stored in said spring member during dose setting. The spring member may, e.g., comprise a spring, such as a compressible spring or a torsion spring, or it may be or comprise any other suitable means capable of storing mechanical energy and subsequently releasing the stored energy. Such an injection device is very easy to use for persons having poor dexterity or low finger strength, e.g. elderly people or children, because only a relatively small force needs to be applied by the user in order to inject a set dose, since the necessary mechanical work is carried out by the spring member. Furthermore, in injection devices where the injection is performed by releasing energy previously stored in a spring member, the piston rod is normally moved during injection by applying a pushing force to the piston rod in a substantially axial direction.

The injection device may further comprise a release mechanism for releasing energy stored in the spring member, thereby causing a set dose to be injected. The release mechanism may, e.g., comprise a release button which the user operates. The release mechanism is preferably axially movable, and it may be operable by a user pressing a release button in a substantially axial direction. In this case the release button may be integral with the dose knob.

In another aspect the invention relates to an injection device for injecting a dose of drug, the injection device comprising:
  a housing,
  a dose setting mechanism being operable to set a desired dose, the dose setting mechanism comprising a rotatable dose knob, operation of the dose setting mechanism causing energy to be stored in a spring member,
  an injection mechanism comprising a piston rod adapted to cooperate with a piston positioned in a cartridge containing a drug to be delivered in order to cause a set dose to be delivered from the cartridge via the injection device, the injection mechanism being driven by releasing energy previously stored in the spring member during dose setting,
  a locking nut being axially fixed relatively to the housing, said locking nut being adapted to be rotationally locked relatively to the housing during dose setting, and being adapted to be able to perform rotational movement relatively to the housing during injection of a set dose, said locking nut being threadedly engaged to the piston rod via a first thread connection,
  a dosage tube being threadedly connected to the piston rod via the first thread connection, said dosage tube being axially movable relatively to the housing during dose setting and during injection of a set dose, and
  means for preventing rotational movement of the piston rod during dose setting.

It should be noted that the remarks set forth above and the features described above in combination with the first aspect of the invention are also applicable in combination with this additional aspect of the invention. Similarly, the remarks set forth below are also applicable in combination with the first aspect of the invention.

According to this additional aspect the locking nut is axially fixed relatively to the housing. Furthermore, it is rotationally locked relatively to the housing during dose setting, but able to rotate relatively to the housing during injection. Thus, the locking nut is completely fixed relatively to the housing during dose setting, and it can perform a purely rotational movement relatively to the housing during injection. The locking nut is threadedly engaged to the piston rod via a first thread connection. Accordingly, the piston rod can only move axially relatively to the housing by either spiralling through the first thread connection and/or by rotating the locking nut. During dose setting the locking nut is not able to rotate, and since the piston rod is prevented from performing rotational movements during dose setting, the piston rod is axially locked during dose setting. During injection the locking nut is allowed to rotate, and the piston rod is therefore able to move axially while rotating the locking nut.

The rotational relationship between the locking nut and the piston rod described above provides the possibility of controlling the axial position of the piston rod in a very accurate manner, including stopping movements of the piston rod, in particular axial movements, in a very accurate manner. This is because the rotational movement provides a larger relative movement between the locking nut and the piston rod per unit length of axial movement of the piston rod, as compared to the case where a total or partial linear movement between the locking nut and the piston rod occurs. Accordingly, a specific axial position of the piston rod corresponds to a relative rotational position between the locking nut and the piston rod, the relative rotational position allowing a somewhat larger tolerance while still ensuring that the axial position is very accurately defined. This is a great advantage because it is thereby possible to avoid the need for producing the controlling mechanism in a very precise manner, i.e. with very low tolerances. This reduces the manufacturing costs without compromising the accuracy.

Thus, a simple and reliable mechanism for accurately controlling the axial position of the piston rod in a spring driven injection device has been provided, and the mechanism functions even if the movement of the piston rod during injection is provided by pushing the piston rod in a substantially axial direction.

The dose setting mechanism comprises a rotatable dose knob, and the injection device comprises a dosage tube being threadedly connected to the piston rod via the first thread connection. The dosage tube is axially movable relatively to the housing during dose setting and during injection of a set dose. The dosage tube is preferably connected to the dose knob in such a manner that it performs a rotational movement when the dose knob is rotated. Since the piston rod is prevented from rotating during dose setting as described above, the dosage tube is thereby caused to advance along the piston rod via the first thread connection. This movement may advantageously be used for storing energy in the spring member, e.g. by compressing a compressible spring. The stored energy is released during injection, the stored energy thereby causing an axial movement of the piston rod during injection.

The dosage tube may further be threadedly connected to the dose knob via a second thread connection. Thereby the dosage tube will be advanced along the second thread connection as well as along the first thread connection during dose setting. As a consequence, the rotational angle by which the dosage tube is rotated during dose setting as compared to the dose knob is equal to the ratio between the pitch of the first thread connection and the pitch of the second thread connection. The dosage tube will typically be rotated a smaller angle than the rotational angle of the dose knob. When the set dose is subsequently injected, the dosage tube will be rotated the 'remaining angle' in the sense that the accumulated angle rotated during dose setting and injection is equal to the rotated angle of the dose knob. Thereby the pitch of the first thread connection can be increased by decreasing the ratio between the pitch of the first thread connection and the pitch of the second thread connection, in order to ensure that the locking nut will be able to rotate during injection.

As an alternative, the dosage tube may be connected to the dose knob via a key and groove connection. According to this embodiment, the dosage tube is simply rotated along with the dose knob during dose setting, and the dosage tube and the dose knob are allowed to perform relative axial movements.

As described above, the means for preventing rotational movement of the piston rod may comprise a key and groove connection between the piston rod and a member being fixed relatively to the housing, or the means for preventing rotational movement of the piston rod may comprise a third thread connection provided between the piston rod and a member being fixed relatively to the housing.

In the latter case, the piston rod will move in the following manner during injection. As the piston rod is pushed in an axial direction, it is forced to rotate relatively to the housing along the third thread connection. Accordingly, the locking nut is caused to rotate due to the rotation of the piston rod as well as due to the first thread connection between the piston rod and the locking nut. As a consequence, the locking nut is rotated more than would be the case if it was rotated due to only one of the reasons stated above. Thereby, the certainty that the locking nut will actually rotate in a proper manner during injection and under given circumstances is increased, due to the higher pitch of the first thread connection. If the locking nut does not rotate properly during injection, the piston rod is prevented from moving axially, and the injection device thereby jams. Thus, the embodiment described above reduces the risk of jamming of the injection device, due to the higher pitch of the first thread connection. A consequence of this is that the injection device according to this embodiment is less vulnerable to operation failure due to dust or dirt entering the injection device.

In the case that the injection device comprises the second thread connection as well as the third thread connection, the pitch of the second thread connection may advantageously be identical to the pitch of the third thread connection. Thereby it is obtained that the dosage tube and the piston rod do not rotate relatively to each other during injection. This provides the possibility of using an end of the piston rod for the purpose of detecting how much medicament there is left in the cartridge, thereby preventing that a dose is set which is higher than the amount of medicament remaining in the cartridge, a so-called 'end-of-content' detection.

BRIEF DESCRIPTION OF THE DRAWINGS

The invention will now be described in further detail with reference to the accompanying drawings in which.

DETAILED DESCRIPTION OF THE DRAWINGS

Figure 1:
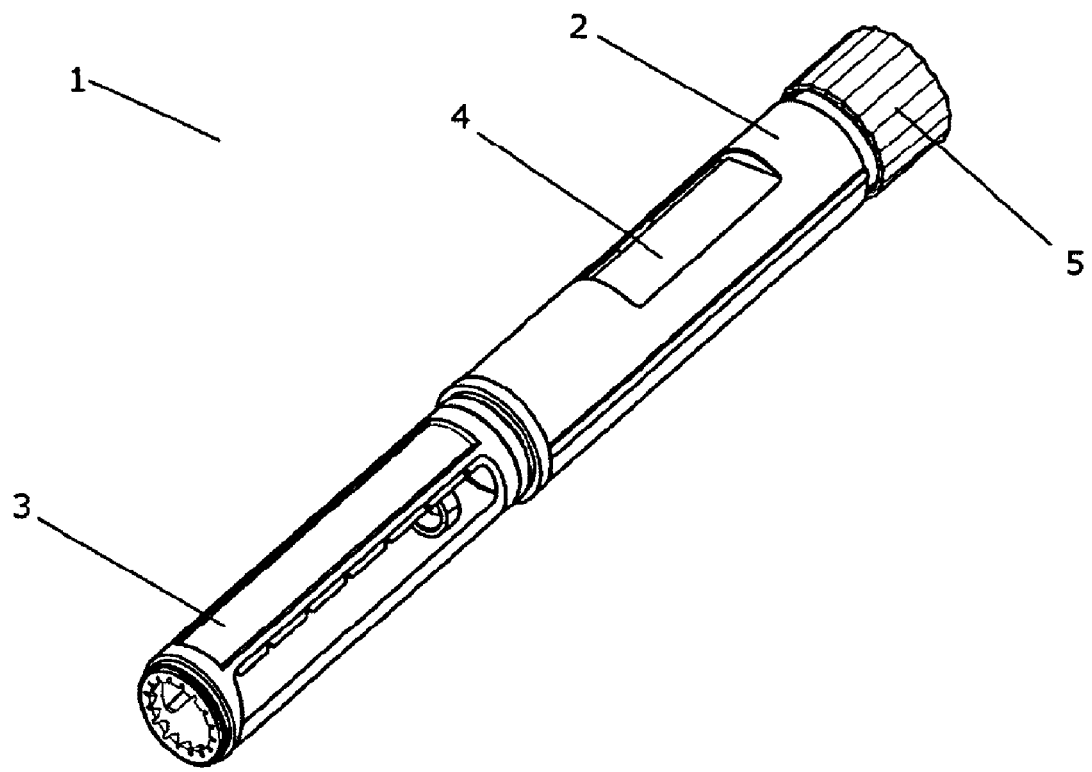
FIG. 1 is a perspective view of an injection device according to a first embodiment of the invention.

FIG. 1 is a perspective view of an injection device 1 comprising a housing with a first part 2 for holding a dose setting mechanism and an injection mechanism, and a second part 3 for holding a cartridge containing a drug to be injected by means of the injection device 1. The first part 2 of the housing is provided with a display 4 which may be used for displaying, e.g., a set dose, the kind of medication contained in the cartridge and/or other relevant information.

The injection device 1 further comprises a dose knob 5 which may be rotated by a user in order to set a desired dose. The operation of the injection device 1 will be described below with reference to FIGS. 2-8.

Figure 2:
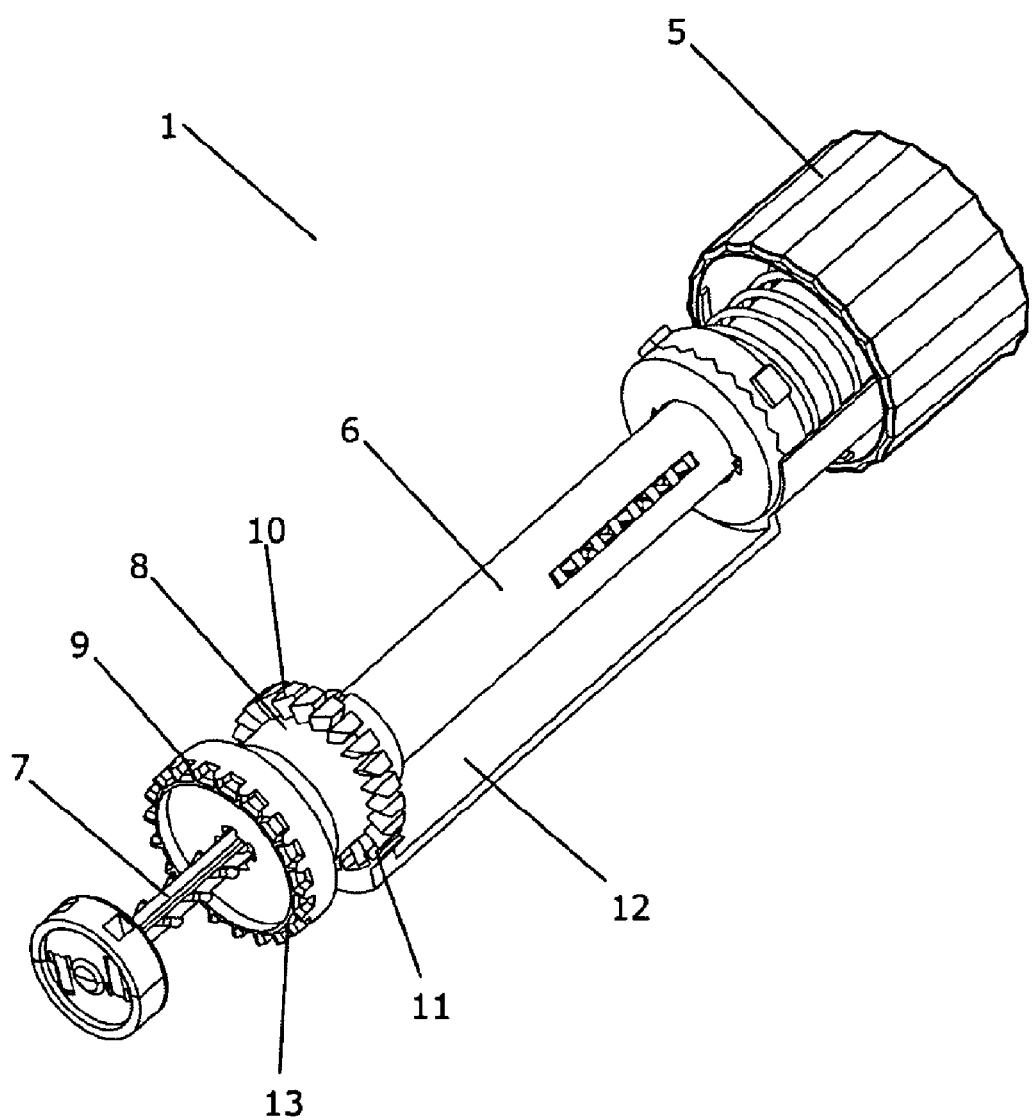
FIG. 2 is a perspective view of the injection device of FIG. 1 with parts removed, the injection device being in a position where it is ready to set a dose.

FIG. 2 is a perspective view of the injection device of FIG. 1. For the sake of clarity, and in order to allow parts arranged in the interior of the injection device 1 to be seen, parts which are not essential for explaining the operation of the injection device 1, including the housing, have been removed. The injection device 1 is in a position where it is ready to set a dose.

The injection device 1 comprises a dosage tube 6 being operatively connected to the dose knob 5 in a manner which will be explained further below, and a piston rod 7 being adapted to cooperate with a piston arranged in a cartridge (not shown) in order to expel a set dose of medication. Furthermore, the injection device 1 comprises a locking nut 8 and a rotational locking item 9.

The locking nut 8 may be locked against rotational movement relatively to the housing by means of a set of teeth 10 arranged on the locking nut 8 engaging a mating set of teeth 11 arranged on a locking item 12. In FIG. 2 the teeth 10, 11 are engaged. The locking item 12 is axially movable, and the teeth 10, 11 may thereby be moved out of engagement, the locking nut 8 thereby being allowed to rotate relatively to the housing. This will be explained further below. During operation of the injection device 1, the locking nut 8 does not move axially relatively to the housing.

During normal operation of the injection device 1, the rotational locking item 9 is locked against rotation relatively to the housing by means of a set of teeth 13 engaging a corresponding set of teeth (not shown) arranged, e.g., on the housing, a cartridge holder or a separate item. However, during change of cartridge the teeth 13 are moved out of engagement, thereby allowing rotational movement of the rotational locking item 9 relatively to the housing, in order to allow the piston rod 7 to return to an initial position.

The locking nut 8 and the rotational locking item 9 are both threadedly connected to the piston 7, but not via the same thread connection. This will be described further below.

Figure 3:
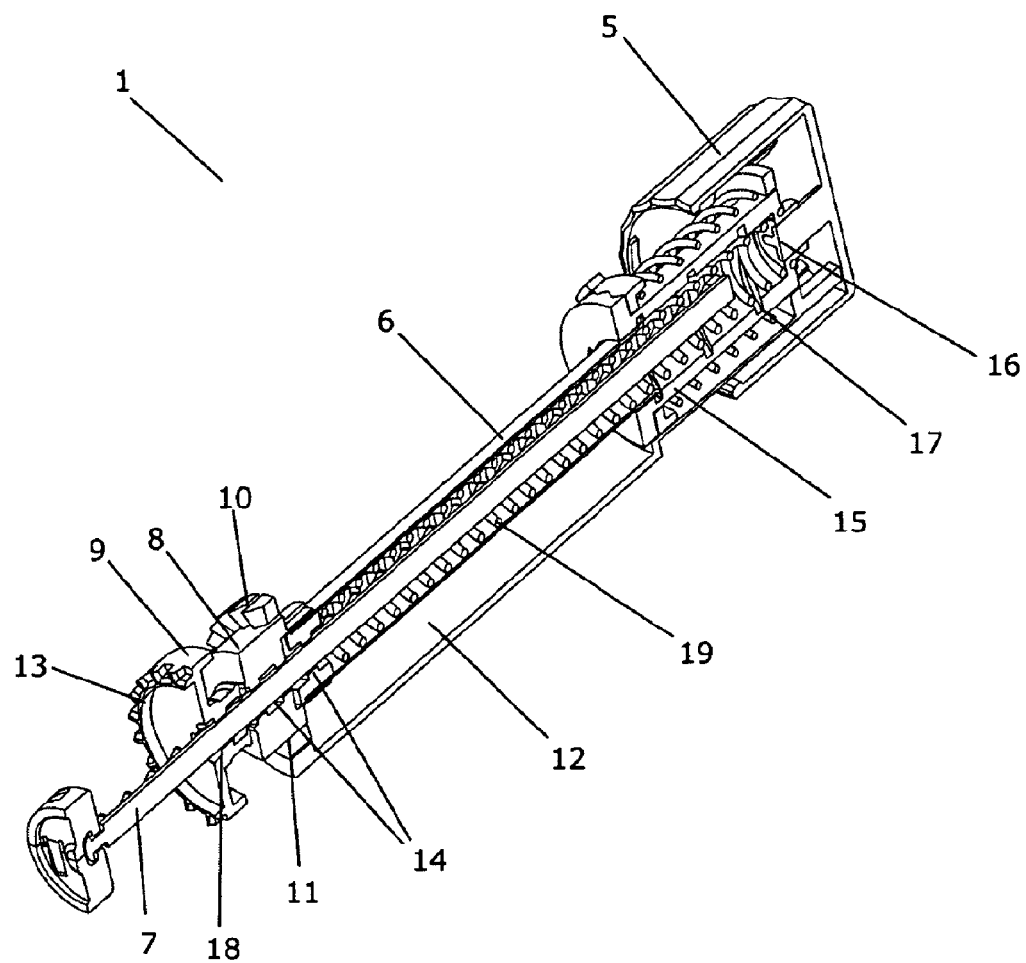
FIG. 3 is a cut through the injection device of FIG. 2.

FIG. 3 is a cut through the injection device 1 shown in FIG. 2. The locking nut 8 and the dosage tube 6 are threadedly connected to the piston rod 7 via a first thread connection 14. When it is desired to set a dose, the operator rotates the dose knob 5. The dose knob 5 is rotationally locked to a dose setting item 15 via connection 16. Accordingly, rotating the dose knob 5 causes the dose setting item 15 to rotate. The dose setting item 15 is provided with an inner thread providing a second thread connection 17 between the dose setting item 15 and the dosage tube 6. Accordingly, rotating the dose setting item 15 causes the dosage tube 6 to climb the second thread connection 17. This takes place in the following manner. As mentioned above, the dosage tube 6 and the locking nut 8 are threadedly connected to the piston rod 7 via the first thread connection 14. The locking nut 8 is prevented from rotating due to the engagement between teeth 10, 11. Furthermore, the rotational locking item 9 is threadedly connected to the piston rod 7 via a third thread connection 18. The third thread connection 18 has a pitch which is directed in a direction which is opposite to the direction of the pitch of the first thread connection 14. Thereby, and since the rotational locking item 9 is rotationally locked to the housing as mentioned above, the piston rod 7 is prevented from rotating during dose setting, and consequently also prevented from moving axially via one of the thread connections 14, 18. As a consequence, the dosage tube 6 climbs the first thread connection 14, thereby compressing compressible spring 19 arranged inside the dosage tube 6. The distance travelled by the dosage tube 6, and thereby the amount of energy stored in the compressible spring 19, represents the amount of the set dose.

Figure 4:
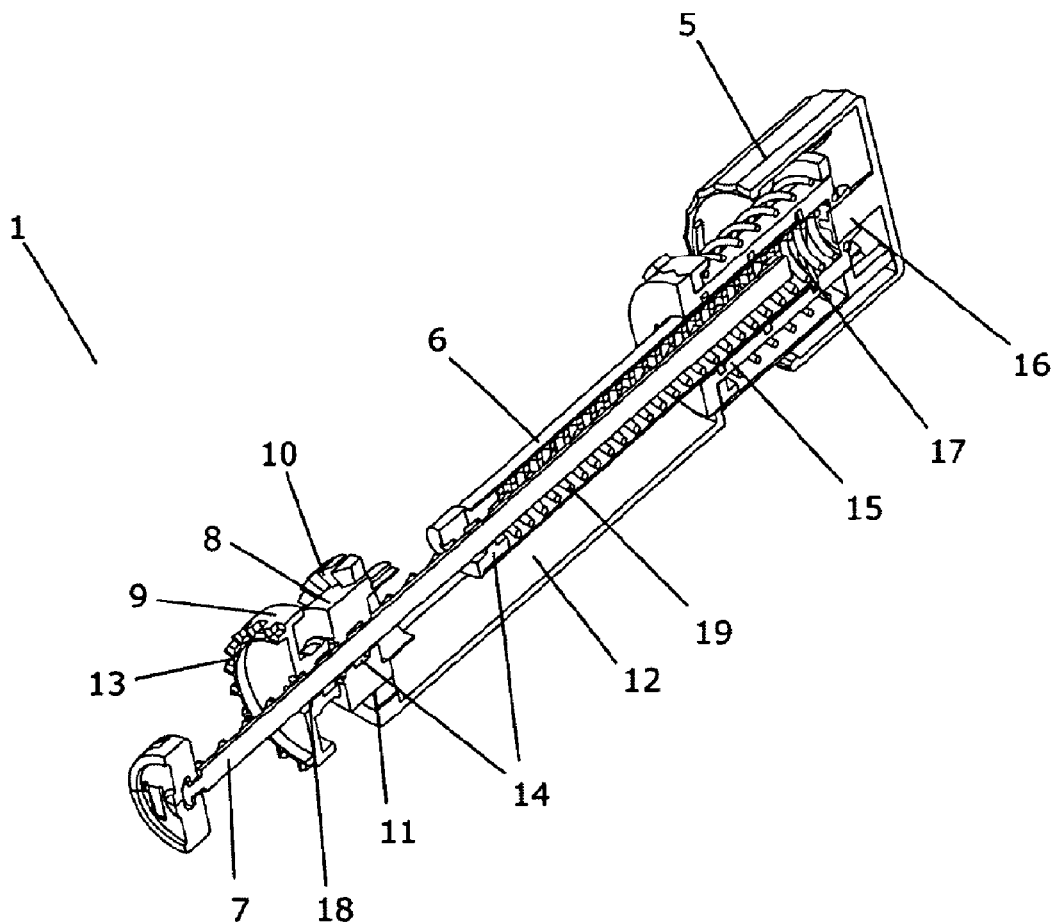
FIG. 4 is a cut through the injection device of FIGS. 1-3, the injection device being in a position where a dose has been set.

FIG. 4 is a cut through the injection device 1 of FIGS. 1-3. The injection device 1 is in a position where a dose has been set as described above. Comparing FIG. 3 and FIG. 4 it is clear that the dosage tube 6 has travelled in a proximal direction via the first thread connection 14 and the second thread connection 17, and that the compressible spring 19 has thereby been compressed.

When it is desired to inject the set dose, the dose knob 5 is pushed in a distal direction, i.e. in a direction towards the piston rod 7. Thereby the locking item 12 will also be pushed in a distal direction. This has the consequence that the teeth 10, 11 are moved out of engagement, and thereby the locking nut 8 is allowed to rotate. However, the locking nut 8 remains axially fixed relatively to the housing.

Figure 5:
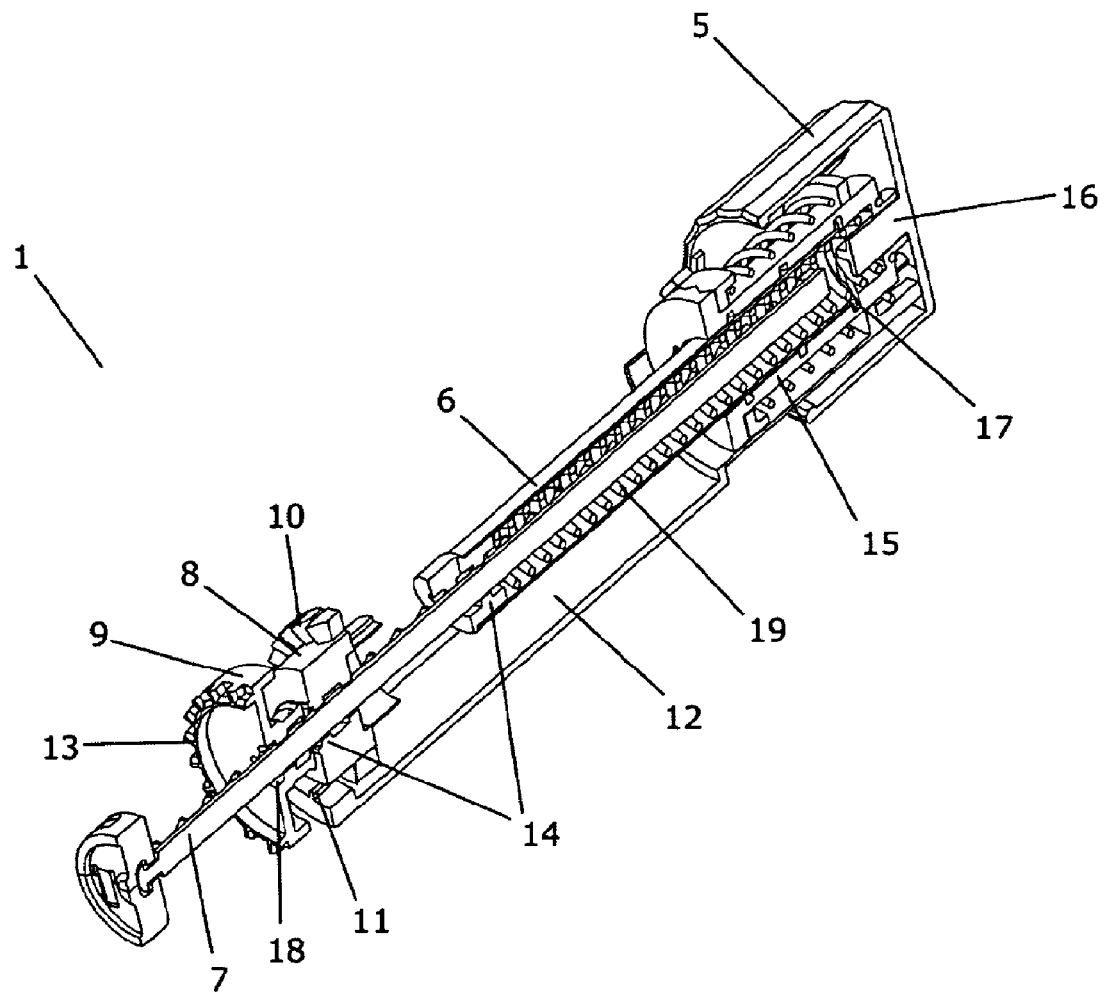
FIG. 5 is a cut through the injection device of FIGS. 1-4, the injection device being in a position where a dose has been set and the injection button has been pushed.

FIG. 5 is a cut through the injection device 1 of FIGS. 1-4. The injection device 1 is in a position where the dose knob 5 has been pushed in a distal direction sufficiently to move the locking item 12 to allow the locking nut 8 to rotate. Comparing FIG. 4 and FIG. 5 it is clear that the locking item 12 has been moved in a distal direction, thereby disengaging the teeth 10, 11. Accordingly, the locking nut 8 is now able to rotate relatively to the housing.

The energy stored in the compressible spring 19 can now be released in the following manner. Since the locking nut 8 is now able to rotate, the piston rod 7 is able to rotate along the third thread connection 18 through the rotational locking item 9. The compressed spring 19 pushes the dosage tube 6 in a distal direction, thereby causing the dosage tube 6 to move along the second thread connection 17 and causing the piston rod 7 move in a distal direction via the third thread connection 18. The axial movement of the piston rod 7 causes it to cooperate with a piston of a cartridge (not shown), and the set dose is thereby injected.

During this the locking nut 8 rotates, and the rotation of the locking nut 8 occurs due to the axial movement of the piston rod 7 in combination with the thread connection 14 between the piston rod 7 and the locking nut 8, as well as due to the rotational movement of the piston rod 7 along the third thread connection 18. Since the resulting rotation of the locking nut 8 is only partly provided due to the thread connection 14 between the locking nut 8 and the piston rod 7, the pitch can be higher as compared to the situation where the pitch engagement must provide the entire rotation. A higher degree of certainty that the locking nut 8 will actually rotate during injection is thereby obtained. If the locking nut 8 accidentally does not rotate during injection, the piston rod 7 is prevented from moving axially, and thereby the injection device 1 will jam. Thus, in the injection device 1 according to this embodiment of the invention, the risk of jamming of the injection device 1 during injection is minimised.

Figure 6:
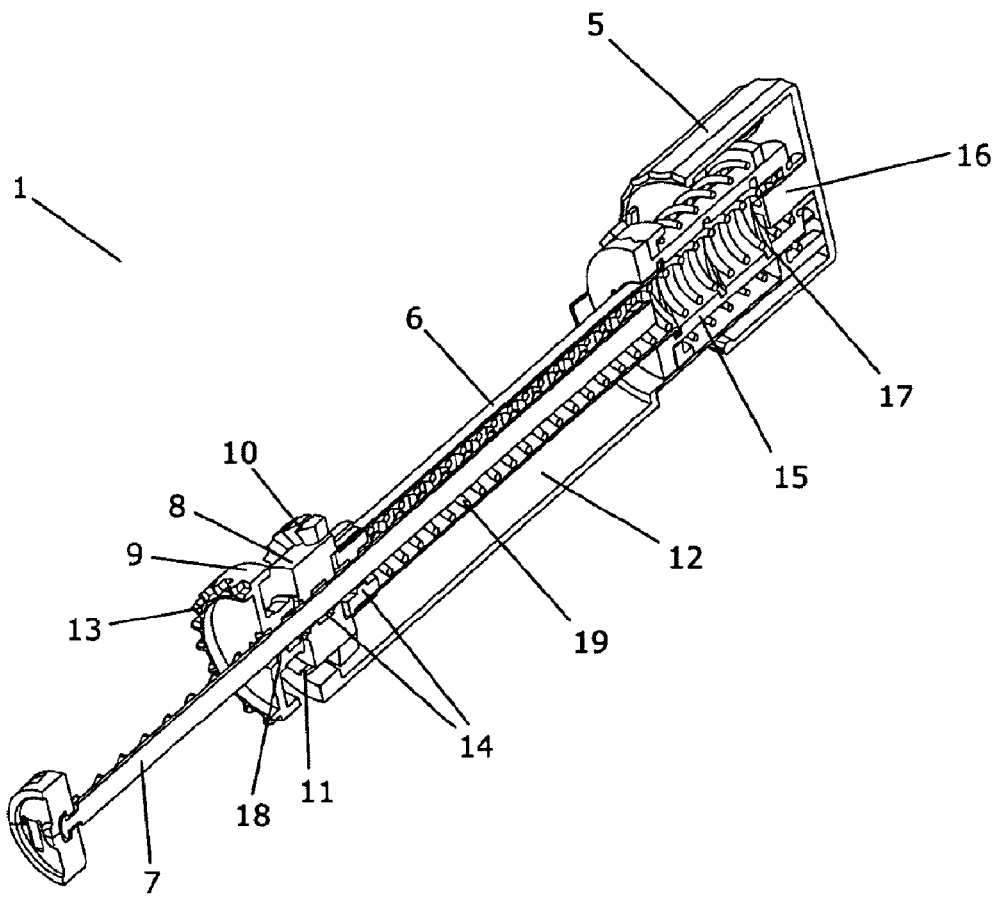
FIG. 6 is a cut through the injection device of FIGS. 1-5, the injection device being in a position where a dose has been injected and the injection button is still pushed.

FIG. 6 is a cut through the injection device 1 of FIGS. 1-5. The injection device 1 is in a position where a dose has just been injected as described above. Comparing FIG. 5 and FIG. 6 it is clear that the dosage tube 6 has been moved in a distal direction to a position where it abuts the locking nut 8, i.e. to the position of FIG. 3. The abutment could be either rotational or axial. Furthermore, comparing FIG. 3 and FIG. 6 it is clear that the piston rod 7 has been moved in a distal direction, thereby indicating that the set dose has been injected. The dose knob 5 is still pushed in, thereby keeping the teeth 10, 11 out of engagement.

Figure 7:
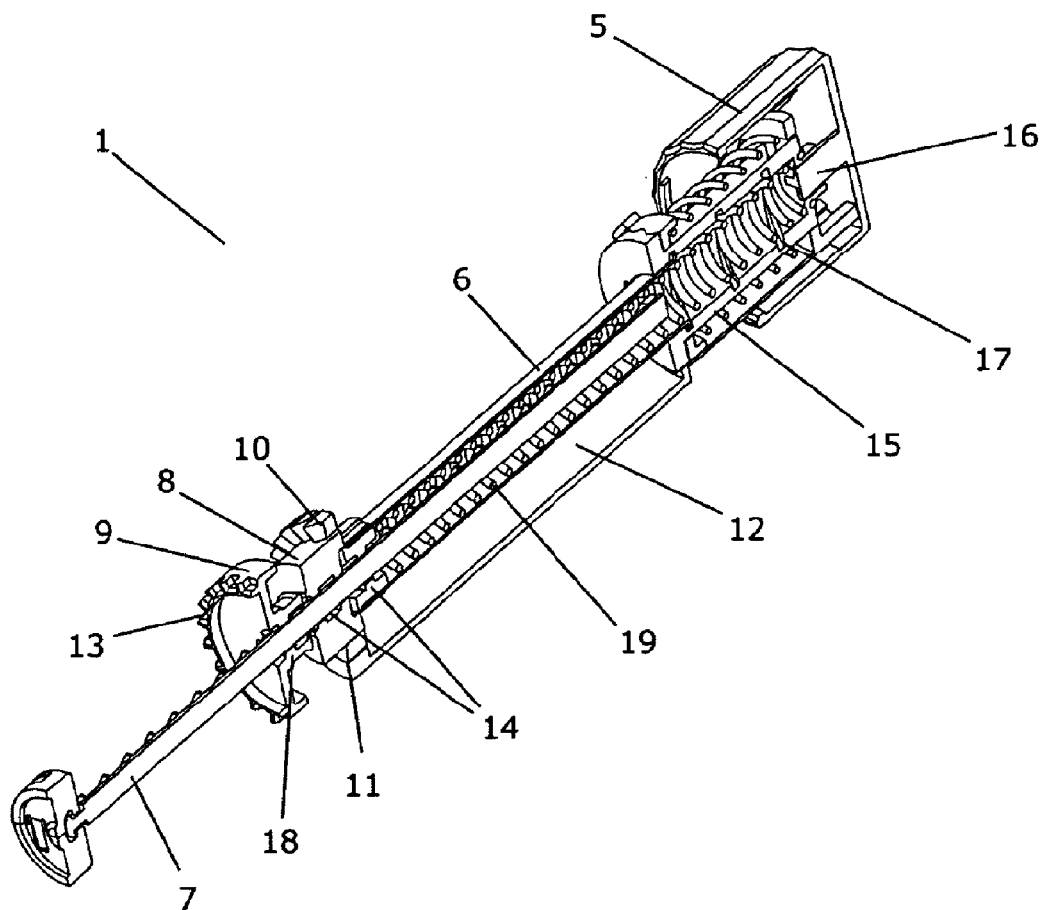
FIG. 7 is a cut through the injection device of FIGS. 1-6, the injection device being in a position where it is ready to set a new dose.

FIG. 7 is a cut through the injection device 1 of FIGS. 1-6. The injection device 1 is in a position where a dose has just been injected and the user has released the dose knob 5. Accordingly, the locking item 12 has been moved back in a proximal direction, thereby causing the teeth 10, 11 to engage. Thus, the injection device 1 shown in FIG. 7 is ready for setting a new dose.

Figure 8:
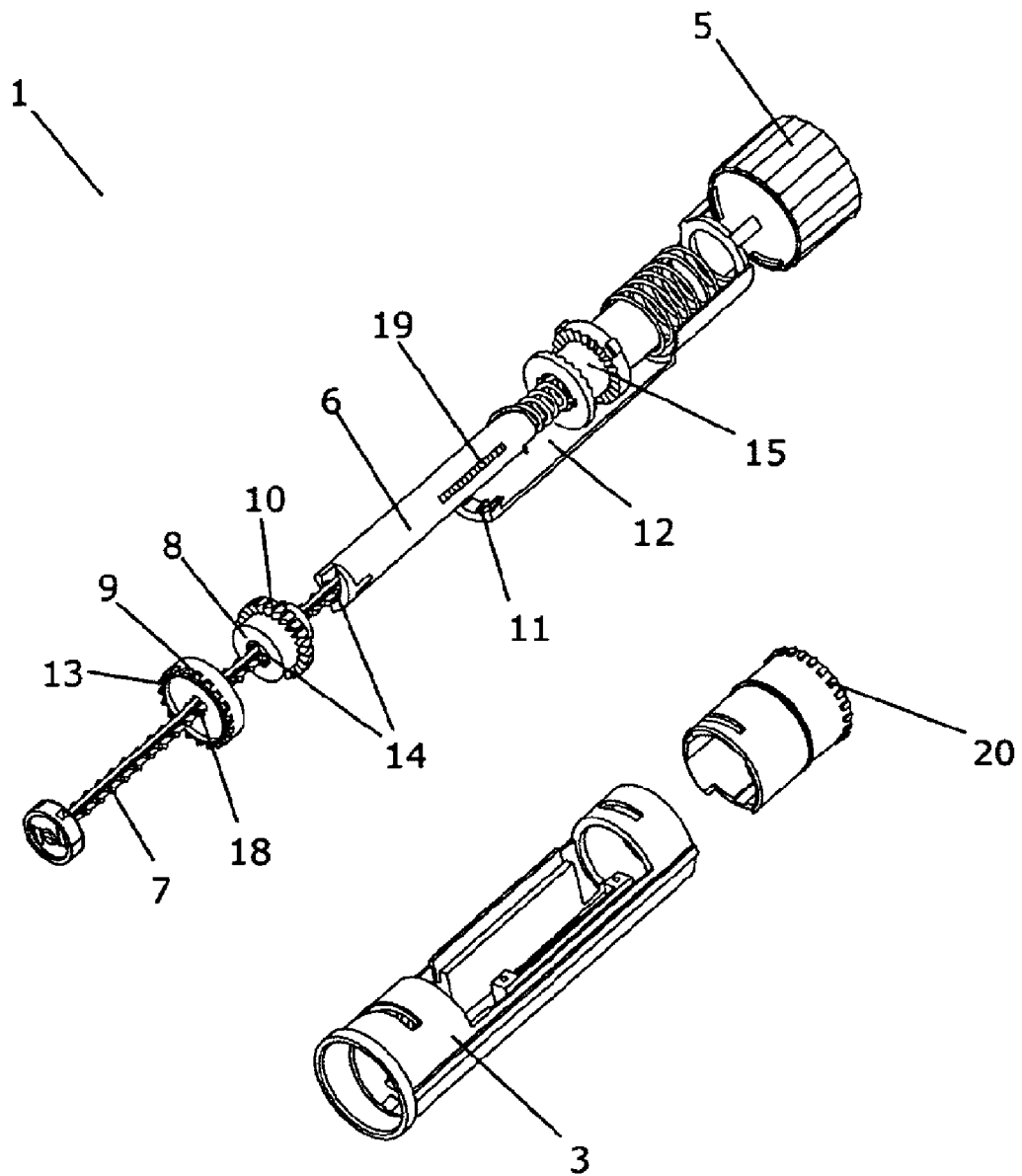
FIG. 8 is an exploded view of selected parts of the injection device of FIGS. 1-7.

FIG. 8 is an exploded view of the injection device 1 of FIGS. 1-7. For the sake of clarity only parts which are necessary for explaining the operation of the injection device 1 are shown. In FIG. 8 mating teeth 20 formed on the housing and being adapted to engage teeth arranged inside the dose knob 5 to prevent the dose knob 5 from rotating during injection are shown.

Figure 9:
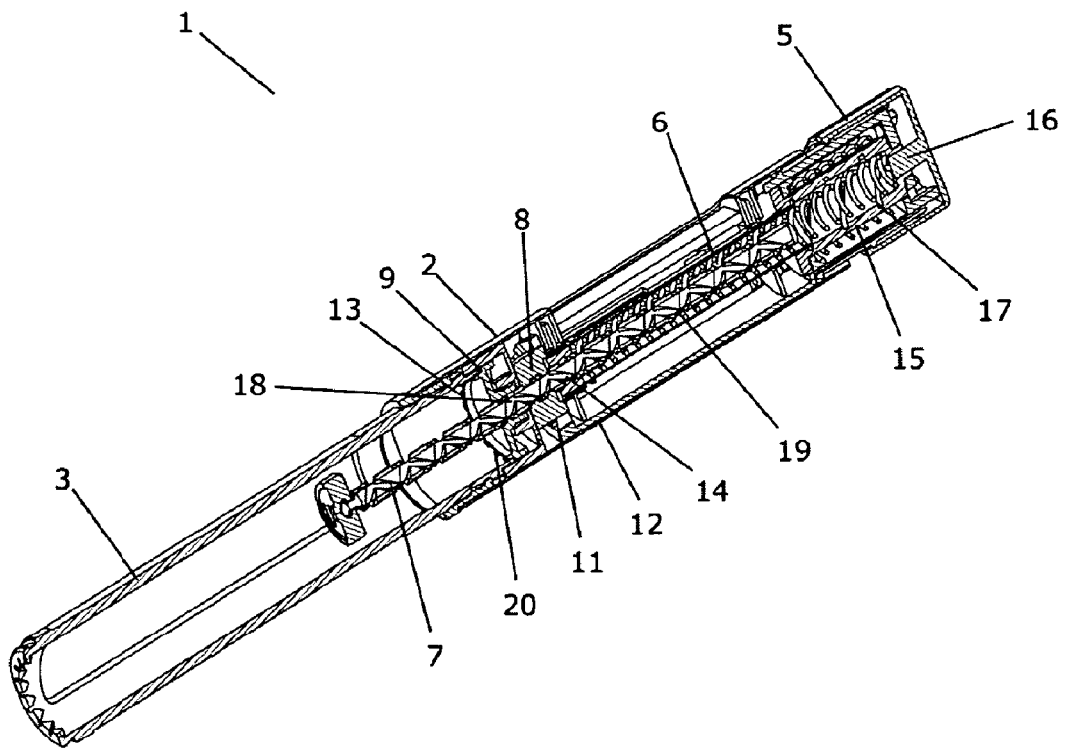
FIG. 9 is a cut through an injection device according to a second embodiment of the invention.

FIG. 9 is a cut through an injection device 1 according to a second embodiment of the invention. The injection device 1 operates very similarly to the embodiment shown in FIGS. 1-8, and like features have therefore been provided with like reference numerals. Furthermore, the basic operation of the injection device 1 will not be described in further detail here.

In FIG. 9 it is clearly seen that the piston rod 7 is provided with two oppositely directed threads 14, 18. One of the threads 14 engages the locking nut 8, and the other thread engages the rotational locking item 9.

The operation of the rotational locking item 9 will now be explained. In FIG. 9 the first part 2 of the housing and the second part 3 of the housing are assembled, i.e. a cartridge (not shown) is positioned in the injection device 1, and the injection device 1 can be operated to set and inject doses of drug as described above. In this situation the teeth 13 arranged on the rotational locking item 9 engage teeth 20 arranged on the second part 3 of the housing. Thereby the rotational locking item 9 is adapted to prevent rotational movement of the piston rod 7 during dose setting as described above.

However, when the cartridge is empty, and thereby needs to be replaced, the first part 2 of the housing and the second part 3 of the housing are detached from each other in order to gain access to the interior of the second part 3 of the housing to replace the cartridge. When the first part 2 of the housing and the second part 3 of the housing are detached, the teeth 13 arranged on the rotational locking item 9 no longer engage the teeth 20 arranged on the second part 3 of the housing. Thus, in this situation, the rotational locking item 9 is allowed to rotate. Accordingly, the piston rod 7 can be pushed back in a direction towards the dose knob 5 in order to allow a new cartridge to be inserted in the injection device 1, rotating the rotational locking item 9 due to the thread engagement between the piston rod 7 and the rotational locking item 9, and due to the rotation of the piston rod 7 in the thread connection 14 between the piston rod 7 and the locking nut 8.

Figure 10:
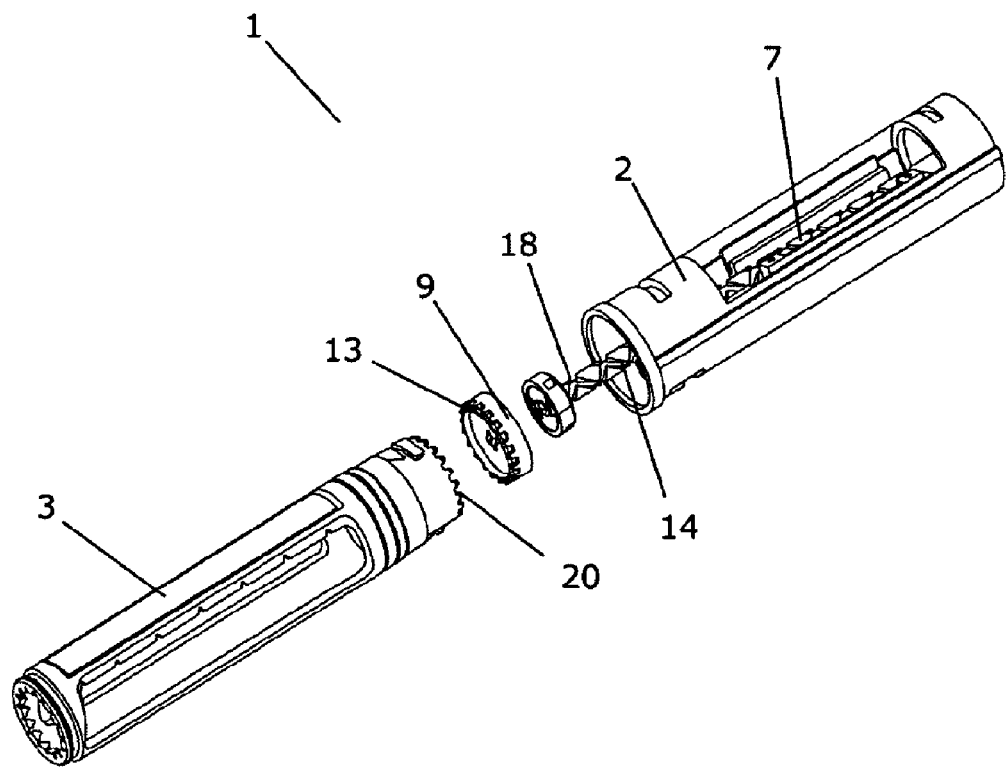
FIG. 10 is an exploded view of the injection device of FIG. 9.

FIG. 10 is an exploded view of the injection device 1 of FIG. 9. FIG. 10 clearly shows the rotational locking item 9 with the set of teeth 13 arranged thereon, and the corresponding set of teeth 20 arranged on the second part 3 of the housing for engaging rotational locking item 9.

Figure 11A:
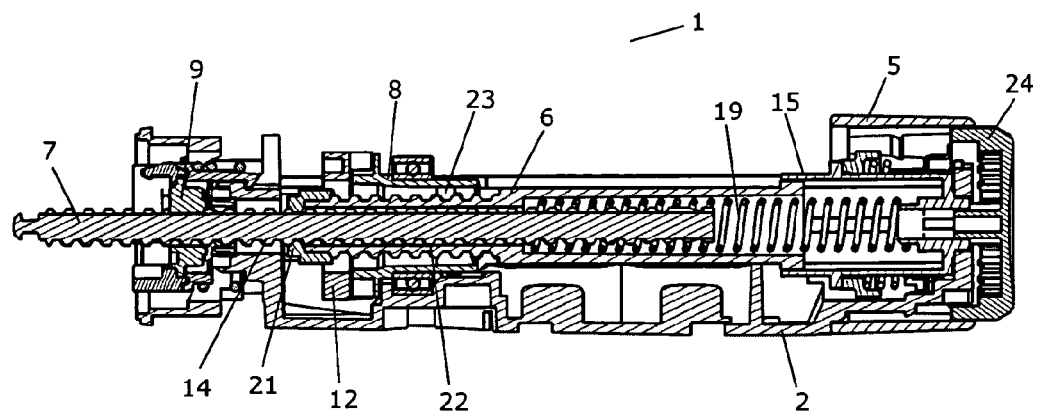
FIG. 11 shows an injection device according to a third embodiment of the invention, the injection device being in a position where it is ready to set a dose.
Figure 11B:
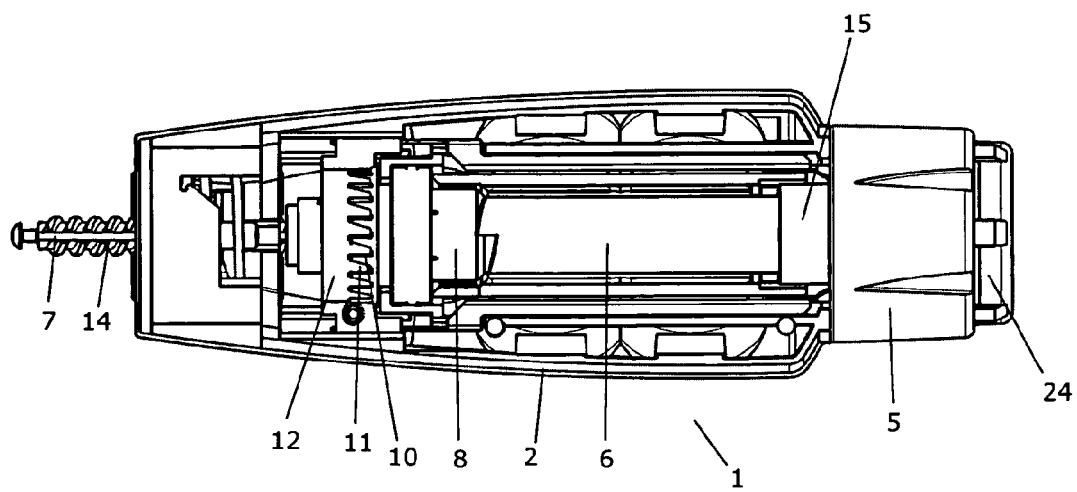

FIGS. 11a and 11b illustrate an injection device 1 according to a third embodiment of the invention. The injection device 1 is shown in a position where it is ready for setting a dose. In FIG. 11a the injection device 1 is shown in a cross sectional view, and in FIG. 11b the injection device 1 is shown in a perspective view with some of the parts omitted for the sake of clarity and in order to show parts arranged in the interior of the injection device and illustrate their operation. The operation of the injection device 1 of FIG. 11 is similar to the operation of the injection devices 1 of FIGS. 1-8 and FIGS. 9-10, respectively, and similar parts have been provided with identical reference numerals.

The injection device 1 of FIG. 11 comprises a dosage tube 6, a piston rod 7 and a locking nut 8. The dosage tube 6 is threadedly connected to the piston rod 7 via inner thread 21 formed on the dosage tube 6 and a corresponding outer thread 14 formed on the piston rod 7. The dosage tube 6 is further provided with an outer thread 22. The dosage tube 6 and the locking nut 8 are threadedly connected via the outer thread 22 of the dosage tube 6 and inner thread 23 formed on the locking nut 8. The outer thread 22 of the dosage tube 6 covers only part of the length of the dosage tube 6. Thereby the distance which the dosage tube 6 is allowed to travel relatively to the locking nut 8 is limited, and the ends of the outer thread 22 of the dosage tube 6 define end positions of the relative movement between the dosage tube 6 and the locking nut 8. Accordingly, it is not possible to set a dose which is smaller than a dose corresponding to one end position, and it is not possible to set a dose which is larger than a dose corresponding to the other end position.

A set of teeth 10 formed on the locking nut 8 and a set of teeth 11 formed on the locking item 12 engage as can be seen in FIG. 11b. The locking item 12 is rotationally locked to the housing 2, and the engagement of the teeth 10, 11 thereby prevents the locking nut 8 from rotating.

When it is desired to set a dose the dose knob 5 is rotated. The dose knob 5 is rotationally locked to injection button 24 via a first spline connection. The injection button 24 is rotationally locked to dose setting item 15 via a second spline connection. The dose setting item 15 is rotationally locked to the dosage tube 6 via a third spline connection. Accordingly, when the dose knob 5 is rotated, the dosage tube 6 is rotated along. Due to the threaded connection between the dosage tube 6 and the locking nut 8, and because the locking nut 8 is prevented from rotating, due to the engagement between teeth 10, 11, the dosage tube 6 is thereby moved axially in a proximal direction relative to the locking nut 8, and in a spiralling movement. Simultaneously, the dosage tube 6 climbs along the piston rod 7 which remains fixed relative to the housing 2.

This axial movement of the dosage tube 6 causes compressible spring 19 to be compressed, i.e. energy is stored in the compressible spring 19. The distance travelled by the dosage tube 6 corresponds to the dose being set.

An initially set dose may be dialled down by reversing the direction of rotation of dose knob 5. The injection device 1 may include an indexing mechanism whereby the dose knob 5 is configured to move in discrete rotational steps corresponding to the desired dose increments. Such an indexing mechanism may be provided as a spring biased click-mechanism.

In some embodiments, the force originating from the compressible spring 19, when compressed, may tend to automatically dial down an initially set dose. However, the inclusion of an indexing mechanism may prevent this by adequately designing the indexing mechanism to provide reluctance against self-returning of the dose knob 5.

Figure 12A:
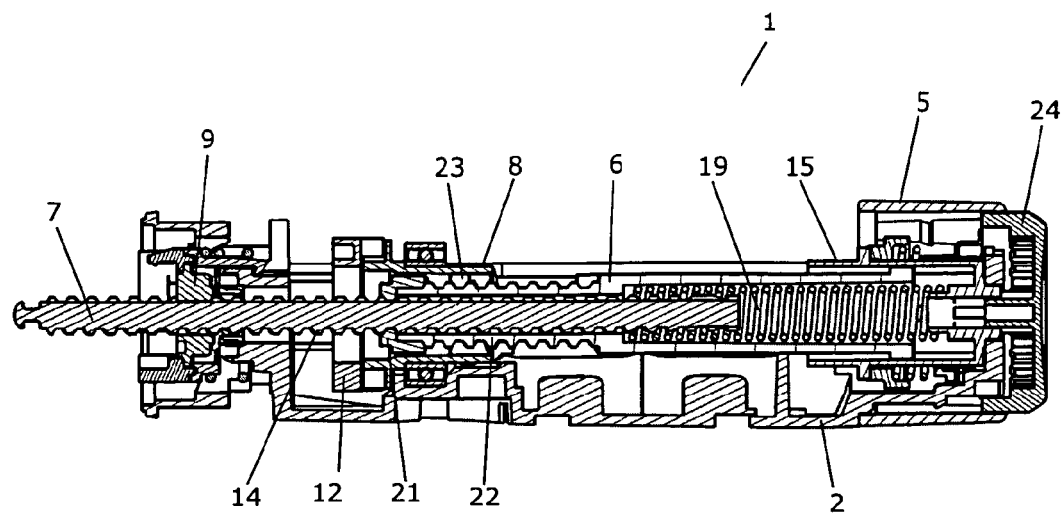
FIG. 12 shows the injection device of FIG. 11 in a position where a dose has been set.
Figure 12B:
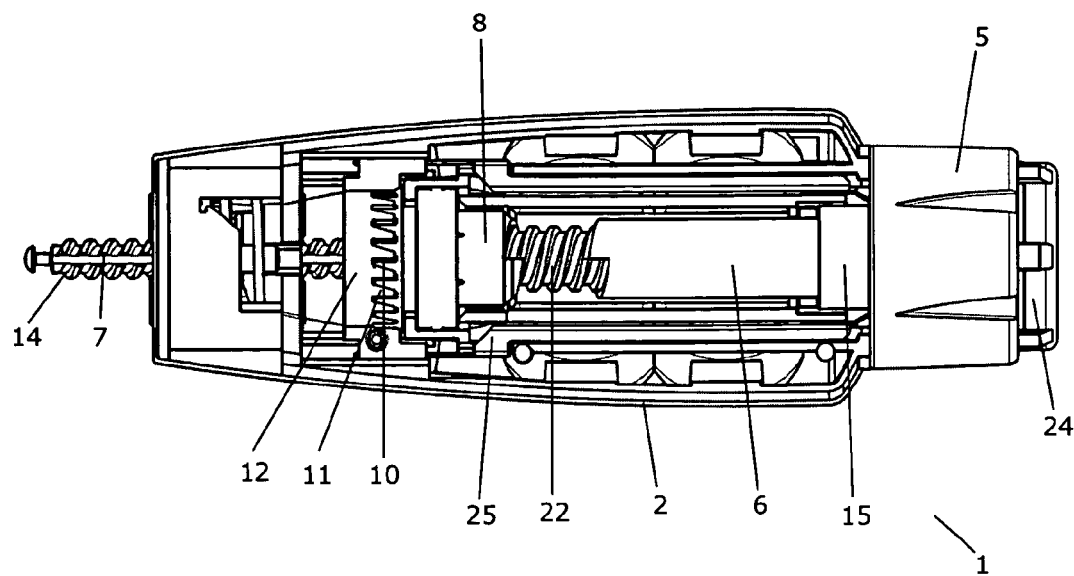

FIGS. 12a and 12b show the injection device 1 of FIG. 11 in a position where a dose has been set. In FIG. 12a the injection device 1 is shown in a cross sectional view, and in FIG. 12b the injection device 1 is shown in a perspective view with some of the parts omitted for the sake of clarity, similar to FIG. 11b.

Comparing FIG. 11 and FIG. 12 it is clear that the dosage tube 6 has been moved in a proximal direction and that the compressible spring 19 has been compressed. In FIG. 12a it can be seen that the dosage tube 6 is arranged in such a manner that the inner thread 23 of the locking nut 8 is positioned very close to one of the ends of the outer thread 22 of the dosage tube 6. Thus, the dose which has been set is very close to the maximum settable dose. In FIG. 12b the outer thread 22 of the dosage tube 6 is visible.

In FIG. 12b it can be seen that the teeth 10 formed on the locking nut 8 and the teeth 11 formed on the locking item 12 are still engaged, i.e. the locking nut 8 is still prevented from rotating relatively to the hosing 2. Thus, the dosage tube 6 is retained in the position shown in FIG. 12.

When it is desired to inject the set dose, the injection button 24 is pushed in a distal direction, i.e. towards the housing 2. The injection button 24 is connected to the locking item 12 via connecting part 25. Accordingly, pushing the injection button 24 causes the locking item 12 to move along in a distal direction, thereby moving the teeth 10, 11 out of engagement, allowing the locking nut 8 to rotate. The injection button 24 is configured in such a manner that it automatically returns to its initial distal position when external pressure acting on the injection button 24 is released.

Figure 13A:
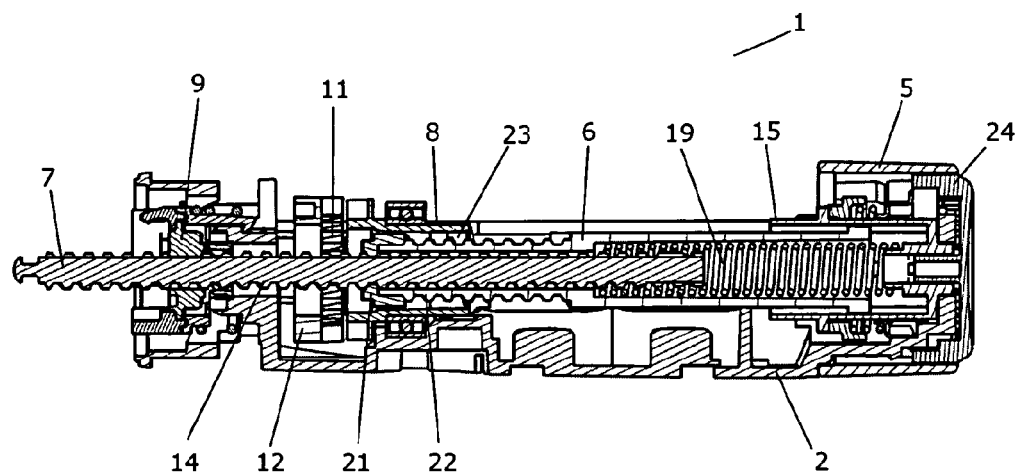
FIG. 13 shows the injection device of FIGS. 11 and 12 in a position where a dose has been set and the injection button has been pushed.
Figure 13B:
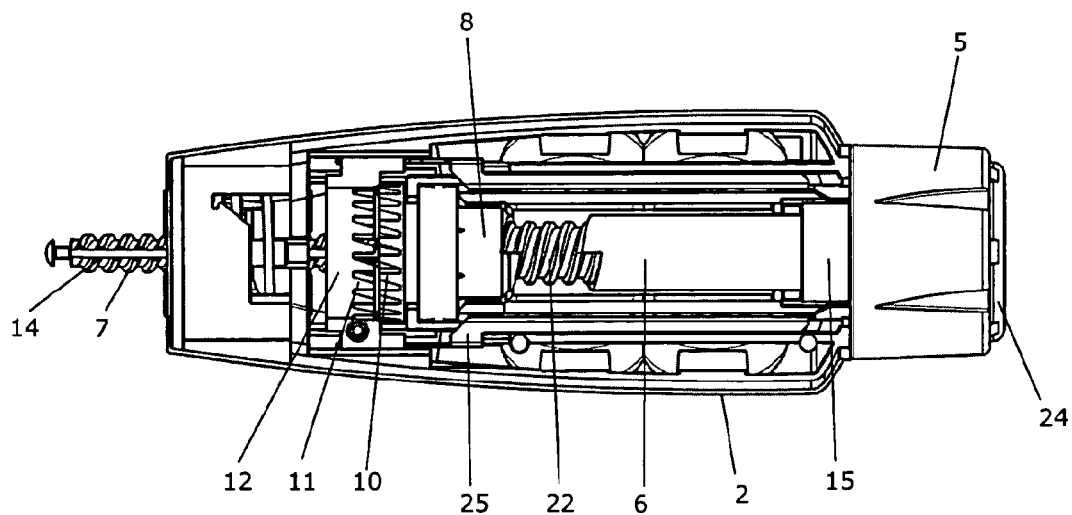

FIGS. 13a and 13b show the injection device 1 of FIGS. 11 and 12 in a position where the injection button 24 has been pushed in a distal direction as described above. In FIG. 13b it can be seen that the teeth 10, 11 have been moved out of engagement. The position of the dosage tube 6 is the same as in FIG. 12, i.e. the injection device 1 has not yet started injecting the set dose.

The compressed spring 19 pushes against the dosage tube 6, thereby urging it in a distal direction. Since the locking nut 8 is now allowed to rotate, the dosage tube 6 is allowed to move in a distal direction, while forcing the locking nut 8 to rotate due to the connection between the outer thread 22 of the dosage tube 6 and the inner thread 23 of the locking nut 8. The energy stored in the compressed spring 19 will cause the dosage tube 6 to perform this movement.

Due to the connection between the inner thread 21 of the dosage tube 6 and the outer thread 14 of the piston rod 7, the piston rod 7 is moved along in this movement. The piston rod 7 is arranged in abutment with a piston (not shown) arranged in a cartridge. Accordingly, moving the piston rod 7 as described above causes the set dose of drug to be expelled from the injection device 1. The injection movement may be halted at any time during injection by releasing the injection button 24. The dose movement may be continued by once again pushing the injection button 24 in the distal direction.

In the shown embodiment, the injection button 24 is provided with a plurality of axially extending teeth (not shown) arranged to releasably engage corresponding teeth (not shown) formed in the housing 2. The engagement of the two sets of teeth is initiated upon pressing in of the injection button 24, and the engagement is released when the injection button 24 moves into its proximal position. Hence, manipulation of the dose knob 5 to alter a set dose during the injection movement is prevented.

Figure 14A:
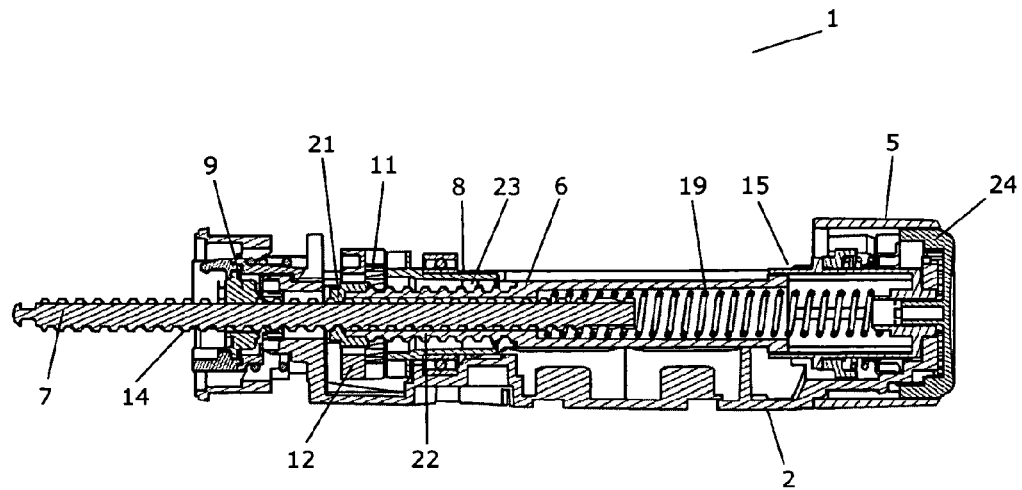
FIG. 14 shows the injection device of FIGS. 11-13 in a position where a dose has been injected and the injection button is still pushed.
Figure 14B:
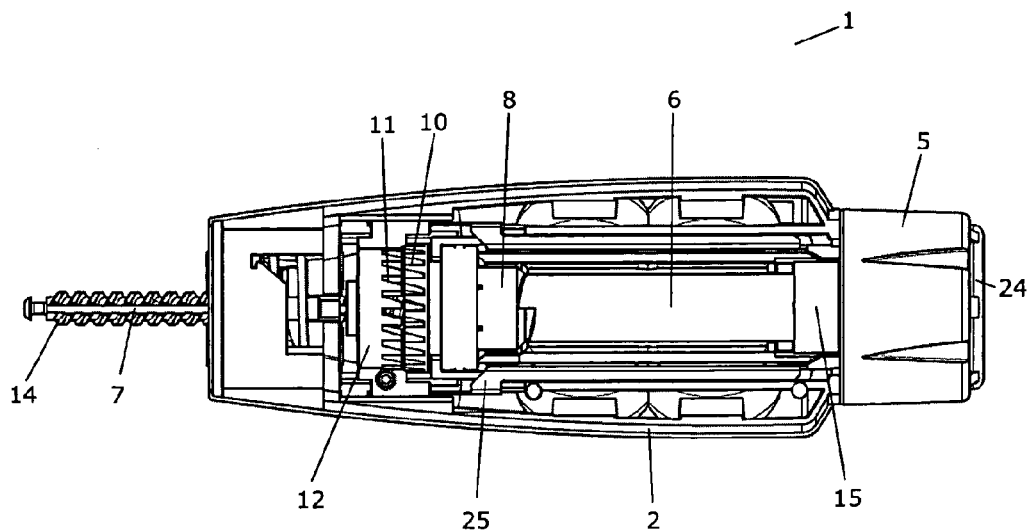

FIGS. 14a and 14b show the injection device 1 of FIGS. 11-13 in a position where injection of the set dose has been completed. Comparing FIG. 13 and FIG. 14 it can be seen that the dosage tube 6 has been returned to the position shown in FIG. 11. However, the piston rod 7 has been moved in a distal direction as compared to the position shown in FIG. 11, thereby indicating that a dose has been injected.

In the shown third embodiment, the piston rod 7 is rotationally locked with respect to the housing 2 during dose setting and injection operations. However, in an alternative embodiment, the piston rod 7 may be configured to rotate during the dosing movement in the same way as described in connection with the first and second embodiment.

Figure 15:
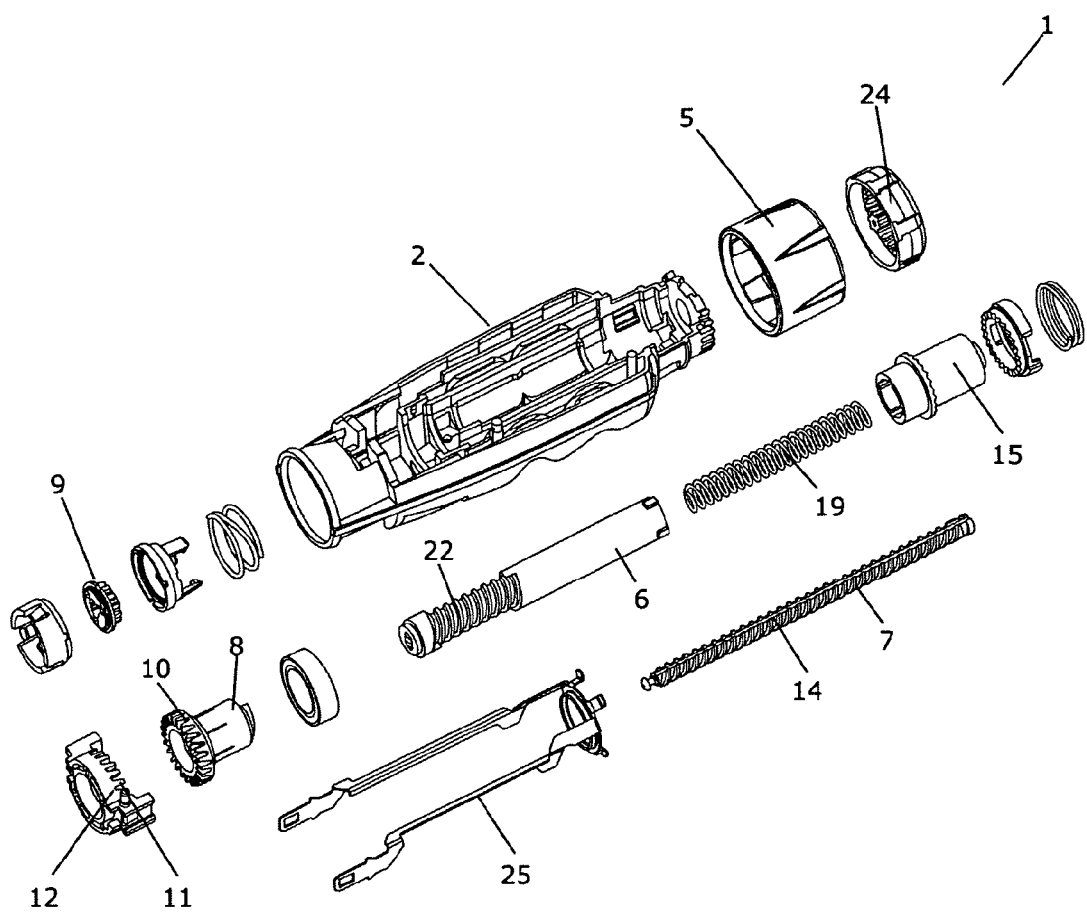
FIG. 15 is an exploded view of selected parts of the injection device of FIGS. 11-14.

FIG. 15 is an exploded view of the injection device 1 of FIGS. 11-14. For the sake of clarity, only the parts necessary for explaining the operation of the injection device 1 are shown. In FIG. 15 the connecting part 25 is clearly visible.

The invention claimed is:

1. An injection device for injecting a dose of drug, the injection device comprising:
   a housing,
   a dose setting mechanism being operable to set a desired dose, the dose setting mechanism comprising a rotatable dose knob, operation of the dose setting mechanism causing energy to be stored in a spring member,
   an injection mechanism comprising a piston rod adapted to cooperate with a piston positioned in a cartridge containing a drug to be delivered in order to cause a set dose to be delivered from the cartridge via the injection device, the injection mechanism being driven by releasing energy previously stored in the spring member during dose setting,
   a dosage tube being axially movable in a proximal direction relatively to the housing during dose setting and being axially movable in a distal direction relatively to the housing during injection of a set dose, and
   retaining means is a locking nut being axially fixed relatively to the housing, said locking nut being adapted to be rotationally locked relatively to the housing during dose setting, and adapted to be able to perform rotational movement relatively to the housing during injection of a set dose, the retaining means arranged to prevent axial movement of the dosage tube in a distal direction relatively to the housing during dose setting.

2. An injection device according to claim 1, wherein the locking nut and the dosage tube are connected via mating threads formed on the dosage tube and the locking nut, respectively.

3. An injection device according to claim 1, further comprising a locking item being movable between a locking position in which it prevents the locking nut from rotating relatively to the housing, and an unlocking position in which the locking nut is allowed to rotate relatively to the housing.

4. An injection device according to claim 3, wherein mating teeth formed on the locking nut and the locking item engage when the locking item is in the locking position.

5. An injection device according to claim 3, wherein the locking item is moved from the locking position to the unlocking position in response to operation of the injection mechanism.

6. An injection device according to claim 1, wherein the dosage tube is prevented from performing rotational movements relatively to the housing during injection of a set dose.

7. An injection device according to claim 1, wherein the dosage tube and the piston rod are connected via mating threads formed on the dosage tube and the piston rod, respectively.

8. An injection device according to claim 1, further comprising means for preventing rotational movement of the piston rod during dose setting.

9. An injection device according to claim 8, wherein the means for preventing rotational movement of the piston rod comprises a key and groove connection between the piston rod and a member being fixed relatively to the housing.

10. An injection device according to any of claim 8, wherein the means for preventing rotational movement of the piston rod comprises a third thread connection provided between the piston rod and a member being fixed relatively to the housing.

11. An injection device according to claim 10, wherein the third thread connection has a pitch being directed in a direction which is opposite to the direction of the outer thread of the piston rod engaging the inner thread of the dosage tube.

12. An injection device according to claim 1, wherein the spring member is or comprises a compressible spring.

13. An injection device according to claim 1, further comprising a release mechanism for releasing energy stored in the spring member, thereby causing a set dose to be injected.

14. An injection device according to claim 13, wherein the release mechanism is axially movable.

\* \* \* \* \*

UNITED STATES PATENT AND TRADEMARK OFFICE
CERTIFICATE OF CORRECTION

Page 1 of 1

PATENT NO. : 8,353,878 B2
APPLICATION NO. : 12/532337
DATED : January 15, 2013
INVENTOR(S) : Moller et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 541 days.

Signed and Sealed this
Eleventh Day of November, 2014

Michelle K. Lee
*Deputy Director of the United States Patent and Trademark Office*